United States Patent
Liu et al.

(10) Patent No.: US 7,553,964 B2
(45) Date of Patent: Jun. 30, 2009

(54) CYCLOBUTYL AMINE DERIVATIVES

(75) Inventors: Huaqing Liu, Buffalo Grove, IL (US); Arthur A. Hancock, Libertyville, IL (US); Kathryn J. Hancock, legal representative, Libertyville, IL (US); Marlon D. Cowart, Round Lake Beach, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/444,825

(22) Filed: Jun. 1, 2006

(65) Prior Publication Data

US 2007/0078133 A1    Apr. 5, 2007

Related U.S. Application Data

(60) Provisional application No. 60/687,357, filed on Jun. 3, 2005.

(51) Int. Cl.
| | |
|---|---|
| C07D 237/08 | (2006.01) |
| C07D 213/02 | (2006.01) |
| C07D 291/04 | (2006.01) |
| C07D 291/06 | (2006.01) |
| C07D 291/08 | (2006.01) |
| C07D 285/06 | (2006.01) |
| C07D 285/08 | (2006.01) |
| C07D 285/10 | (2006.01) |
| C07D 285/12 | (2006.01) |
| C07D 285/22 | (2006.01) |
| C07D 285/20 | (2006.01) |
| C07D 277/22 | (2006.01) |

(52) U.S. Cl. .................. 544/239; 546/329; 548/122; 548/123; 548/124; 548/125; 548/206; 548/215

(58) Field of Classification Search .............. 544/239, 544/244
See application file for complete search history.

(56) References Cited

U.S. PATENT DOCUMENTS

| | | |
|---|---|---|
| 6,515,013 B2 | 2/2003 | Bennani et al. |
| 6,620,839 B2 | 9/2003 | Bennani et al. |
| 2005/0171181 A1* | 8/2005 | Wager et al. ............... 514/408 |
| 2008/0021081 A1 | 1/2008 | Liu et al. |

FOREIGN PATENT DOCUMENTS

| | | |
|---|---|---|
| EP | 0259977 | 8/1987 |
| WO | 94/15928 | 7/1994 |
| WO | 95/20588 | 3/1995 |
| WO | 00/44728 | 8/2000 |
| WO | 02/074758 | 9/2002 |
| WO | 2004/043458 | 5/2004 |
| WO | 2005/080361 | 9/2005 |

OTHER PUBLICATIONS

Prodrug [online], [retrieved on Mar. 26, 2007]. Retrieved from the internet, URL; http://en.wikipedia.org/wiki/Prodrug>.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Cecil Textbook of Medicine, $20^{th}$ edition (1996), vol. 2, pp. 1992-1996.*
Cecil Textbook of Medicine, $20^{th}$ edition (1996), vol. 2, pp. 2050-2057.*
Arrang, J.-M., et al., "Auto-inhibition of brain histamine releas mediated by a novel class ($H_3$) of histamine receptor", Nature, 302:832-837 (1983).
Arrang, J.-M., et al., "Highly potent and selective ligands for histamine $H_3$-receptors", Nature, 327:117-123 (1987).
Barbier, A.J., et al., "Acute wake-promoting actions of JNJ-5207852, a novel, diamine-based $H_3$ antagonist", Br. J. of Pharm., 143:649-661 (2004).
Bernaerts, P., et al., "Histamine H3 antagonist thioperamide dose-dependently enhances memory consolidation and reverse amnesia induced by dizocilpine or scopolamine in a one-trail inhibitory avoidance task in mice", Beh. Brain Res., 154:211-219 (2004).
Bjenning, C., et al., "Peripherally adminstered Ciproxifan elevates Hypothalamic Histamine Levels and Potently Reduces Food intake in the Sprague Dawley rat", Hist. Res. In the New Millenium, 499-452 (2001).
Bomann, M.D., et al., "A Mild, Pyridine-Borane-Based Reductive Amination Protocol", J. Org. Chem., 60:5995-5996 (1995).

(Continued)

Primary Examiner—Rebecca L Anderson
Assistant Examiner—Shawquia Young
(74) Attorney, Agent, or Firm—Portia Chen

(57) ABSTRACT

Compounds of formula (I)

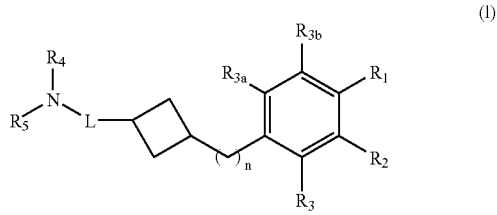

(I)

are useful in treating conditions or disorders prevented by or ameliorated by histamine-3 receptor ligands. Also disclosed are pharmaceutical compositions comprising the histamine-3 receptor ligands, methods for using such compounds and compositions, and a process for preparing compounds within the scope of formula (I).

17 Claims, No Drawings

OTHER PUBLICATIONS

Brady, W.T. & Waters, O.H., "Halogenated Ketenes. V. Cycloadditions of Dichloroketene to Olefins", *J. Org. Chem.*, 32:3703-3705 (1967).

Browman, K.E., et al., "Enhancement of prepulse inhibition of startle in mice by the $H_3$ receptor antagonists thioperamide and ciproxifan", *Beh. Brain Res.*, 153:69-76 (2004).

Chen, Z., "Effects of histamine on MK-801-induced memory deficits in radial maze performance in rats", *Brain Res.*, 839:186-178 (1999).

Chen, Z., et al., "Pharmacological effects of carcinine on histaminergic neurons in the brain", *Br. J. of Pharm.*, 143:573-780 (2004).

Clapham, J. & Kilpatrick, G.J., "Thioperamide, the selective histamine $H_3$ receptor antagonist, attenuates stimulant-induced locomotor activity in the mouse", *Eur. J. of Pharm.*, 259:107-114 (1994).

Cowart, M., et al., "4-(2-[2-(2®-Methylpyrrolidin-1-yl)ethyl]benzofuran-5-yl)benzonitrile and Relate 2-Aminoethylbenzofuran $H_3$ receptor Antagonist Potently Enhance Cognition and Attention", *J. Med. Chem.*, 48:38-55 (2005).

De Almeda, M.A.M.R. & Izquierdo, I., "Memory Facilitation by Histamine", *Arch. Int. Pharmacodyn.*, 283:19-198 (1986).

Dehmlow, E.V. & Büker, S., "Stereoselektive Synthese von 3-substituierten Cyclobutanolen und Folgeprodukten", *Chemische Berichte*, 126:2759-2763 (1993).

Delaunois, A., et al., "Modulation of acetylcholine, capsaicin and substance P effects by histamine $H_3$ receptors in isolated perfused rabit lungs", *Eur. J. of Pharma.*, 277:243-250 (1995).

Dimitriadou, V., et al., "Functional relationship between mast cells and C-sensitive nerve fibres evidenced by histamine $H_3$-receptor modulation in a rat lung and spleen", *Clin. Sci.*, 87:151-163 (1994).

Duméry & Blozovski, D., "Development of amygdaloid cholinergic mediation of passive avoidance learning in the rat", *Exp. Brain Res.*, 67:61-69 (1987).

Dvorak, C.A., et al., 4-Phenoxypiperidines: Potent, Conformationally Restricted, Non-Imidazole Histamine $H_3$ Antagonists, *J. Med. Chem.*, 48:2229-2238 (2005).

Esbenshade, T.A., et al., "Pharmacological and Behavioral properties of A-349821, a selective and potent human histamine $H_3$ receptor antagonist", *Biochem. Pharm.*, 68:933-945 (2004).

Falmagne, J.-B., "Cyclobutanone and cyclobutenone Derivative by Reaction of Tertiary Amides with Alkenes or Alkynes", *Angew. Chem. Int. Ed. Engl.*, 20(10):879-880 (1981).

Fitzsimons C., et al., "Histamine receptors signaling in epiderman tumor cell lines with H-*ras* gene alterations", *Inflamm. Res.*, 747(Supl 1):S50-S51 (1998).

Fox, G.B., et al., "Effects of histamine $H_3$ receptor ligands GT-2331 and ciproxifan in a repeated acquisition avoidance response in the spontaneously hypertensive rat pup", *Beh. Brain Res.*, 131:151-161 (2002).

Fox, G.B., et al., "Two Novel and Selective Nonimidazole $H_3$ Receptor Antagonists A-304121 and LA-317920: II. In Vivo Behavioral and Nuerophysiological characterization", *J. of Pharm. & Exp. Ther.*, a305(30:897-908 (2003).

Fox, G.B., et al., Identification of novel $H_3$ receptor ($H_3$R)antagonists with cognition enhancing properties in rats:, *Inflamm. Res.*, 52(Suppl. 1):S31-S32 (2003).

Fox, G.B., et al., "Pharmacological Properties of ABT-239 [4-(2-{2-[(2R)-2-Methylpyrrolidinty]lethal}-benzofuran-5-yl)benzonitrile]: II Neurophysiological Characterization and Broad Preclinical Efficacy in Cognition and Schizophrenia of a Potent and Selective Histamine $H_3$ Receptor Antagonists", *J. of Pharm. & Exp. Ther.*, 313(1):176-190 (2005).

Furniss, B.S., et al., "Vogel's Textbook of Practical Organic Chemistry", 5th Ed.:Table of Contents (1989).

Ghosez, L., et al., "Intramolecular Cycloadditions of Keteniminium Salts. A Novel Apporach Toward Prostaglandins", *Tetrahedron Ltrs.*, 27(43):5211-5214 (1986).

Glase, S.A., et al., "Chapter 2. Attention Deficit Hyperactivity Disorder: Pathophysiology and Design of New Treatments", *Ann. Rep. In Medic. Chem.*, 37:11-20 (2002).

Halpern, M.T., "GT-2331 Gliatech, Inc.", *Curr. Opin. In CPNS Invest. Drugs*, 1(4):524-527 (1999).

Hancock, A. A., et al "Antiobesity effects of A-331440, an novel non-imidazole histamine $H_3$ receptor Antagonist", *Eur. J. of harm.*, 487:183-197 (2004).

Hancock, A.A., et al., "Histamine $H_3$ antagonists in models of obesity", *Inflamm. Res.*, 53(Suppl. 1):S47-S48 (2004).

Harada, C., et al., "Inhibitory effect of iodophenpropit, a selective histamine $H_3$ antagonist, on amygdaloid kindled seizures", *Brain Res. Bull.*, 63:143-146 (2004).

Houge, C., et al., "Models for Asymmetric [2+2] Cycloadditions", *J. Am. Chem. Soc.*, 104:2920-2921 (1982).

Hriscu, A., et al., "Evaluarea Experimentala a Eficacitatii Analgezice a Unor Antihistaminice, Ca Dovada a Implicarii receptorilor Histaminergici in Patogenia Dureprii", *Farmacia*, XLIX(2):23-30 & 76 (2001).

Huang, Y .-W., et al., "Effect of the histamine $H_3$-antagonist clobenpropit on spatial memory deficits induced by MK-801 as evaluated by radial maze in Sprague-Dawley rats", *Beh. Brain Res.*, 151:287-293 (2004).

Itoh, E., et al., "Thioperamide, a Histamine $H_3$ Receptor Antagonist, Powerfully Suppresses Peptide YY-Induced Food Intake in Rats", *Biol. Psychiatry*, 45:475-481 (1999).

"Rules for the Nomenclature of Organic Chemistry", *IUPAC Commission on Nomenclature of Org. Chem.*, Section E:13-30 (1974).

Kamei, C., et al., "Influence of certain $H_1$ -blockers on the step-through active avoidance response in rats", *Psychopharmacology*, 102:312-318 (1990).

Kamei, C. & Tasaka, K., "Participation of Histamine in the Step-Through Active Avoidance Response and Its Inhibition by $H_1$-Blockers", *Japan J. Pharmacol.*, 57:473-482 (1991).

Kauffmann, T., et al., "Home Aldehydselektivitat Bei Carbonylolefinierungen MIT Titan- Und Chrom-Reagenzien (1)", *Tetradehron Ltrs.*, 22(50):5031-5034 (1981).

Komater, V.A., et al., "$H_3$ raeceptor blockade by thioperamide enhances cognition in rats without inducing locomotor sensitization", *Psychopharmacology*, 67:363-372 (2003).

Krepski, L.R. & Hassner, A., "An Improved Procedure for the Addition of Dichloroketene to Unreactive Olefins",*J. Org. Chem.*, 43(14):2879-2882 (1978).

Kurukami, K., et al., "AQ-0145, a Newly Developed Histamine $H_3$ Antagonist, Decreased Seizure Susceptibility of Electrically Induced Convulsions in Mice", *Meth. Find Exp. Clin. Pharmacol.*, 17 © :70-73 (1995).

Lamberti, C., et al., "Antidepressant-like effects of endogenous histamine and of two histamine $H_1$ receptor agaonists in the mouse forced swim test", *Br. J. of Pharmacology*, 123:1331-1336 (1998).

Leurs, R. & Timmerman, H., "The histamine $H_3$-receptor: A target for developing new drugs", 127-165 (1998).

Leurs, R. et al., "The medicinal chemistry and therapeutic potentials of ligands of the histamine $H_3$ receptor", *Prog. In Drug Res.*, 45:107-165 (1995).

Li, S.-W., et al., "A Novel Methylenation Method of Aldehydes Mediated by Dibutyl Telluride", *Chem. Ber.*, 123:1441-1442 (1990).

Ligneau, X., et al., "Neurochemical and Behavioral Effects of Ciproxifan, A Potent Histamine $H_3$-Receptor Antagonist",*J. of Pharmacology & Exper. Ther.*, 287(2):658-666 (1998).

Lin, J.-S., et al., "Involvement of histaminergic neurons in arousal mechanisms demonstrated with $H_3$-receptor ligands in the cat", *Brain Res.*, 523:325-330 (1990).

Lozada, A.F., et al., "Plasticity of histamine $H_3$receptor expression and binding in the vestibular nuclei after labyrinthectomy in rat", *BMC Neuroscience*, 5:32 (2004).

Malmberg'Aiello, P., et al., "Role of histamine in rodent antinociception", *Br. J. Pharmacol.*, 111:1269-1279 (1994).

Markóet al., "Intramolecular [2+2] Cycloadditions of Ketenes and Keteniminium Salts to Olefins", *J. Am. Chem. Soc.*, 107:2192-2194 (1985).

Mazurkiewicz-Kwilecki, I.M., & Nsonwah, S., "Changes in the regional brain histamine and histidine levels in postmortem brains of Alzheimer patients", *Can. J. Physiol. Pharmacol.*, 67:75-78 (1989(.

McLeod, R.L., et al. "Combined Histamine $H_1$ and $H_3$ Receptor Blockade Produces Nasal Decongestion in an Experimental Model of Nasal Congestion", *Am. J. of Rhinology*, 13(5):391-399 (1999).

McLeod, R.L., et al., "Histamine $H_3$ Antagonists", *Prog. In Resp. Res.*, 31:133-136 (2001).

Meguro, K.-I., et al., Effects of thioperamide, a Histamine $H_3$ Antagonist, on the Step-Through Passive Avoidance Response and Histidine Decarboxylase Activity in Sensescence-Accelerated Mice, *Pharmacol. Biochem. Beh.*, 50(3):321-325 (1995).

Monti, J.M., et al., "Effects of selective activation or blockade of the histamine $H_3$ receptor on sleep and wakefulness", *Eur. J. of Pharmacol.*, 205:283-287 (1991).

Monti, J.M., et al., "Sleep and Waking during Acute Histamine $H_3$ Agonist BP 2.94 or $H_3$ Antagonist Carboperamide (MR 16155) Administration in Rats", *Neuropsychopharmacology*, 15(1):31-35 (1996).

Morisset, S., et al., "Atypical Neuroleptics Enhance Histamine Turnoer in Brain Via 5-Hydroxytryptamino$_{2A}$ Receptor Blockade", *J. of Pharmacol. & Exp. Ther.*, 288(2):590-596 (1999).

O'Neill, A.B., et al., "Pharmacological Evaluation of an In Vivo Model of Vestibular Dysfunction in the Rat", *Meth. Find Exp. Clin. Pharmacol.*, 21(4):285-289 (1999).

Onodera, K., et al., "Neuropharmacology of the Histaminergic Neuron System in the Brain and Its Relationship with Behavioral Disorders", *Progr. In Neurobiol.*, 42:685-702 (1994).

Onodera, K., et al., "Improvement by FUB 181, a novel histamine $H_3$-receptor antagonist, of learning and memory in the elevated plus-maze test in mice", *Naunyn-Schmiedeberg's Arch. Pharmacol.*, 357:508-513 (1998).

Pan, J.B., et al., "Histaminergic Ligands Attenuate Barrel Rotation in Rats Following Unilateral Labyrinthectomy", *Meth. Find Exp. Clin. Pharmacol.*, 20(9):771-777 (1998).

Panula, P., et al., "Neuronal Histamine Deficit in Alzheimer's Disease", *Neurosci.*, 82(4):993-997 (1998).

Passani, M.B., et al., "Central histaminergic system and cognition-",*Neurosci. & Biobehav. Rev.*, 24:107-113 (2000).

Pelter, A. & Rosser, R.M., "Reductive Aminations of Ketones and Aldehydes using Borane-Pyridine", *J. Chem. Soc.*, 4:717-720 (1984).

Penning, T.D., et al., "Structure-Activity Relationship Studies on I-[2-(4-Phenylphenoxy)ethyl]pyrrolidine (SC-22716), a Potent Inhibitor of Leukotriene $A_4$ ($LTA_4$) Hydrolase", *J. Med. Chem.*, 43:721-735 (2000).

Perez-Garcia, Carmen, et al., "Effects of histamine $H_3$ receptor ligands in experimental models of anxiety and depression", *Psychopharmacology*, 142:215-220 (1999).

Poste, G., et al., "Lipid Vesicles as Carriers for Introducing Biologically Active Materials into Cells", *Methods in Cell Biology*, XIV:33-70 (1976).

Prast, H., et al., "Histaminergic neurons facilitate social memory in rats", *Brain Res.*, 734:316-318 (1996).

"Pro-drugs as Novel Drug Delivery Systems", *ACS Symposium Series 14*, Table of Cont., 1974).

Pu, Y.-M., et al., "A Facile and Scaleable Synthesis of LABT-239, A benzofuranoid $H_3$Antagonist", *Org. Proc. Res. & Dev.*, 9:45-50 (2005).

Rodrigues, A.A., et al., "Interaction of clozapine with the histamine $H_3$ receptor in rat brain", *Br. J. of Pharmacol.*, 334:1523-1524 (1995).

Sakai, N., et al., "Effects of Thioperamide. A Histamine H.Receptor Antagonist. On Locomotor Activity and Brain Histamine Content in Mast Cell-Deficient w/w Mice", *Life Sci.*, 48:2397-2404 (1991).

Sakata, T., et al., "Hypothalamic neuronal histamine modulates ad libitum feeding by rats", *Brain Res.*, 537:303-306 (1990).

Sanchez-Lemus, E., et al., "Histamine $H_3$ receptor activation inhibits dopamine $D_1$ receptor-induced camp accumulation in rat striatal slices", *Neurosci. Ltrs.*, 364:179-184 (2004).

Schwartz, J.-C., et al., "Histamine", *Psychopharmacology: The Fourth Gen. Of Prog.*, Chapt. 35:397-405 (1995).

Schweitzer, J.B., & Holcomb, H.H., "Drugs under investigation for attention-deficit hyperactivity disorder", *Curr. Opin. In Invest. Drugs*, 3(*8):1207-1211 (2002).

Shah, C., et al., "Novel Human Histamine $H_3$ Receptor Antagonists", *Rioorgan. & Medic. Chem. Ltrs.*, 12:3309-3312 (2002).

Shaywitz, B.A., et al., "Dopaminergic but not noradrenergic mediation of hyperactivity and performance deficits kin the developing rat pup", *Psychopharmacology*, 82:73-77 (1984).

Srivastava, R.R., et al., "4-Dihydroxyborylphenyl Analogues of 1-Aminocyclobutanecarboxylic Acids: Potential Boron Neutron Capture Therapy Agents", *J. Org. Chem.*, 64:8495-8500 (1999).

Szelag, A., "Role of histamine $H_3$-receptors in the proliferation of neoplastic cells in vitro", *Med. Sci. Monit.*, 4(5):747-755 (1998).

Tedford, C.E., et al., "Pharmacvological Characterization of GT-2016, a Non-Thiourea-Containing Histamine $H_3$ Receptor Antagonist: In Vitro and In Vivo Studies", *J. of Pharmacology & Exp. Ther.*, 275(2):598-604 (1995).

Tozer, M.J. & Kalindjian, B., "Histamine H receptor antagonists", *Exp. Opin. Of Ther. Patents*, 10(7):1045-1055 (2000).

Vohora, D., et al., "Thioperamide, A Selective Histamine H.Receptor Antagonist, Protects Against PTZ-Induced Seizures in Mice", *Life Sci.*, 66(22):297-301 (2000).

Wada, H., et al., "Is the histamingergic neuron system a regulatory center for whole-brain activity?", *TINS*, 14(9):415-421 (1991).

Yates, S.L., et al., "Identification and Pharmacological Characterization of a Series of New 1H-4-Substituted-Imidazoyl Histamine $H_3$ Receptor Ligands", *J. of Pharmacol. & Exp. Ther.*, 289(2):1151-1159 (1999).

Yates, S.L., et al., "Effects of a Novel Histamine $H_3$ Receptor Antagonist GT-2394 On Food Intake and Weight Gain in Sprague-Dawley Rats", *Soc. For Neurosci.*, 26:279 (2000).

Yawata, I., et al., "Role of histaminergic neurons in development of epileptic seizures in EL mice", *Mol. Brain Res.*, 132:13-17 (2004).

Yokoyama, H., et al., "Effect of thioperamide, a histamine $H_3$ receptor antagonist, on electrically induced convulsions in mice", *Eur. J. of Pharmacol.*, 234:129-133 (1993).

Yokoyama, H., et al., "Clobenpropit (VUF-9153), a new histamine $H_3$ receptor antagonist, inhibits electrically induced convulsions in mice", *Eur. J. of Pharmacol.*, 260:23-28 (1994).

Yokoyama, H. & Iinuma, K., "Histamine and Seizures-Implications for the Treatment of Epilepsy", *CNS Drugs*, 5(5)):321-330 (1996).

* cited by examiner

CYCLOBUTYL AMINE DERIVATIVES

This application claims the benefit of U.S. Patent Application No. 60/687,357, filed on Jun. 3, 2005, which is hereby incorporated by reference.

BACKGROUND OF THE INVENTION

1. Technical Field

The invention relates to cyclobutyl amine compounds, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302: 832-837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, inverse agonist, agonist, or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to cyclobutyl amines and, more particularly, bicyclic- and tricyclic-substituted cyclobutyl amine derivatives. Accordingly, one aspect of the invention relates to compounds of formula (I):

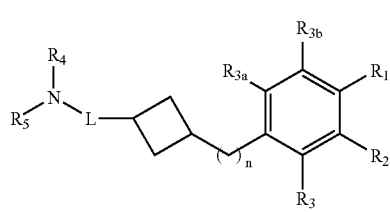

(I)

or a pharmaceutically acceptable salt, ester, amide, or prodrug thereof, wherein:

one of $R_1$ and $R_2$ is a group of the formula -$L_2$-$R_{6a}$-$L_3$-$R_{6b}$;
the other of $R_1$ and $R_2$ is selected from hydrogen, alkyl, alkoxy, halogen, cyano, and thioalkoxy;
$R_3$, $R_{3a}$, and $R_{3b}$ are each independently selected from hydrogen, alkyl, alkoxy, halogen, cyano, and thioalkoxy;
$R_4$ and $R_5$ are each independently selected from alkyl, fluoroalkyl, hydroxyalkyl, alkoxyalkyl, and cycloalkyl, or $R_4$ and $R_5$ taken together with the nitrogen atom to which each is attached form a non-aromatic ring of the formula:

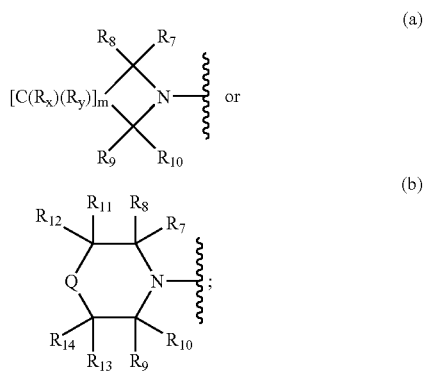

$R_7$, $R_8$, $R_9$, and $R_{10}$ at each occurrence are each independently selected from hydrogen, hydroxyalkyl, fluoroalkyl, cycloalkyl, and alkyl;
$R_{11}$, $R_{12}$, $R_{13}$, and $R_{14}$ are each independently selected from hydrogen, hydroxyalkyl, alkyl, and fluoroalkyl;
$R_{6a}$ is selected from a 5- to 6-membered heteroaryl ring, cyanophenyl, an 8- to 10-membered bicyclic heteroaryl ring, and a 4- to 8-membered heterocyclic ring;
$R_{6b}$ is selected from hydrogen, a 5- to 6-membered heteroaryl ring, phenyl, an 8- to 10-membered bicyclic heteroaryl ring, and a 4- to 8-membered heterocyclic ring;
Q is selected from O and S;
L is —[C($R_{16}$)($R_{17}$)]$_k$;
$L_2$ is selected from a bond, —O—, —C(=O)—, —S—, —NH—, —N($R_{16}$)C(=O)—, —C(=O)N($R_{16}$), and —N(alkyl)—;
$L_3$ is selected from a bond, —O—, —C(=O)—, —S—, —N($R_{16}$)C(=O)—, —C(=O)N($R_{16}$), and —N($R_{15}$)—;
$R_{15}$ is selected from hydrogen, alkyl, acyl, alkoxycarbonyl, amido, and formyl;
$R_{16}$ and $R_{17}$ at each occurrence are independently selected from hydrogen and alkyl;
$R_x$ and $R_y$ at each occurrence are independently selected from hydrogen, hydroxy, alkyl, alkoxy, alkylamino, fluoro, and dialkylamino;
k is 0, 1, or 2;
m is an integer from 1 to 5; and
n is 0 or 1.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to memory and cognition processes, neurological processes, cardiovascular function, and body weight. Accordingly, the compounds and compositions of the invention are useful as a medicament for treating or preventing $H_3$ receptor modulated disease.

Processes for making compounds of the invention also are contemplated.

The compounds, compositions comprising the compounds, methods for making the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means a —$NH_2$ group.

The term "aryl" as used herein means a monocyclic hydrocarbon aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, $NR_AR_B$, and $(NR_AR_B)$sulfonyl.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —$CO_2H$ group, which may be protected as an ester group —$CO_2$-alkyl.

The term "cyano" as used herein means a —CN group.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, oxo, thioalkoxy, and —NR$_A$R$_B$.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing 1, 2, 3, or 4 heteroatoms independently selected from nitrogen, oxygen, or sulfur, or a tautomer thereof. Such rings can be monocyclic or bicyclic as further described herein. Heteroaryl rings are connected to the parent molecular moiety, or to L$_2$ or L$_3$, wherein L$_2$ and L$_3$ are defined in formula (I), through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms are arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,4]thiadiazolonyl, [1,2,5]thiadiazolonyl, [1,3,4]thiadiazinonyl, [1,2,3]oxadiazolyl, [1,2,4]oxadiazolonyl, [1,2,5]oxadiazolonyl, [1,3,4]oxadiazinonyl, thiazolyl, thienyl, [1,2,3]triazinyl, [1,2,4]triazinyl, [1,3,5]triazinyl, [1,2,3]triazolyl, [1,2,4]triazolyl, pyridazinonyl, pyridonyl, and pyrimidinonyl.

The term "bicyclic heteroaryl" or "8- to 10-membered bicyclic heteroaryl ring", as used herein, refers to an 8-, 9-, or 10-membered bicyclic aromatic ring containing at least 3 double bonds, and wherein the atoms of the ring include 1, 2, 3, 4, or 5 heteroatoms independently selected from oxygen, sulfur, and nitrogen. Representative examples of 8- to 10-membered bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, and pyrrolopyrimidinyl.

Heteroaryl groups of the invention, whether monocyclic or bicyclic, can be substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, formyl, haloalkoxy, haloalkyl, halogen, hydroxy, hydroxyalkyl, mercapto, nitro, oxo, thioalkoxy, —NR$_A$R$_B$, (NR$_A$R$_B$)carbonyl, and (NR$_A$R$_B$)sulfonyl. Heteroaryl groups of the present invention that are substituted may be present as tautomers.

The terms "heterocyclic ring" and "heterocycle", as used herein, refer to a four-, five-, six-, seven-, or eight-membered ring containing at least one saturated carbon atom, and also containing one, two, or three heteroatoms independently selected from the group consisting of nitrogen, oxygen, and sulfur. Four- and five-membered rings may have zero or one double bond. Six-membered rings may have zero, one, or two double bonds. Seven- and eight-membered rings may have zero, one, two, or three double bonds. The heterocycle groups of the invention can be attached through a carbon atom or a nitrogen atom. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing heterocycles include, but are not limited to, dioxanyl, dithianyl, tetrahydrofuryl, dihydropyranyl, and tetrahydropyranyl.

The heterocycles of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —NR$_A$R$_B$, and (NR$_A$R$_B$)sulfonyl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "—$NR_AR_B$" as used herein means two groups, $R_A$ and $R_B$, which are appended to the parent molecular moiety through a nitrogen atom. $R_A$ and $R_B$ are independently selected from hydrogen, alkyl, acyl, and formyl. Representative examples of —$NR_AR_B$ include, but are not limited to, amino, dimethylamino, methylamino, acetylamino, and acetylmethylamino.

The term "($NR_AR_B$)alkyl" as used herein means an —$NR_AR_B$ group, as defined herein, appended to the parent molecular moiety through an alkyl group, as defined herein. Representative examples of ($NR_AR_B$)alkyl include, but are not limited to, 2-(methylamino)ethyl, 2-(dimethylamino)ethyl, 2-(amino)ethyl, 2-(ethylmethylamino)ethyl, and the like.

The term "($NR_AR_B$)carbonyl" as used herein means an —$NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, (ethylmethylamino)carbonyl, and the like.

The term "($NR_AR_B$)sulfonyl" as used herein means a —$NR_AR_B$ group, as defined herein, appended to the parent molecular moiety through a sulfonyl group, as defined herein. Representative examples of ($NR_AR_B$)sulfonyl include, but are not limited to, aminosulfonyl, (methylamino)sulfonyl, (dimethylamino)sulfonyl and (ethylmethylamino)sulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O)$_2$C=O, a diaryl anhydride, for example as represented by (aryl-O)$_2$C=O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

Compounds of the Invention

Compounds of the invention can have the formula (I) as described above.

In compounds of formula (I), one of $R_1$ and $R_2$ is a group of the formula -$L_2$-$R_{6a}$-$L_3$-$R_{6b}$. The other group of $R_1$ and $R_2$ is selected from hydrogen, alkyl, alkoxy, halogen, cyano, and thioalkoxy. Preferably, $R_1$ is -$L_2$-$R_{6a}$-$L_3$-$R_{6b}$ and $R_2$ is selected from hydrogen, alkyl, alkoxy, halogen, cyano, and thioalkoxy. When one of $R_1$ or $R_2$ is -$L_2$-$R_{6a}$-$L_3$-$R_{6b}$, then the other is preferably hydrogen.

$L_2$ is selected from a bond, —O—, —C(=O)—, —S—, —NH—, —N($R_{16}$)C(=O)—, —C(=O)N($R_{16}$), and —N(alkyl)-. It is preferred that $L_2$ is a bond.

$L_3$ is selected from a bond, —O—, —C(=O)—, —S—, —N($R_{16}$)C(=O)—, —C(=O)N($R_{16}$), and —N($R_{15}$)—, wherein $R_{15}$ is selected from the group consisting of hydrogen, alkyl, acyl, alkoxycarbonyl, amido, and formyl. It is preferred that $L_3$ is a bond.

$R_{6a}$ is selected from a 5- to 6-membered heteroaryl ring, cyanophenyl, an 8- to 10-membered bicyclic heteroaryl ring, and a 4- to 8-membered heterocyclic ring. The 5- to 6-membered heteroaryl ring, 8- to 10-membered bicyclic heteroaryl ring, and 4- to 8-membered heterocyclic ring for $R_{6a}$ can be substituted or unsubstituted.

$R_{6b}$ is selected from hydrogen, a 5- to 6-membered heteroaryl ring, phenyl, an 8- to 10-membered bicyclic heteroaryl ring, and a 4- to 8-membered heterocyclic ring. The 5- to 6-membered heteroaryl ring, phenyl, 8- to 10-membered bicyclic heteroaryl ring, and 4- to 8-membered heterocyclic ring for $R_{6b}$ can be substituted or unsubstituted.

Specific examples of 5- to 6-membered heteroaryl rings suitable for $R_{6a}$ and $R_{6b}$ include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,4]thiadiazolonyl, [1,2,5]thiadiazolonyl, [1,3,4]thiadiazinonyl, [1,2,3]oxadiazolyl, [1,2,4]oxadiazolonyl, [1,2,5]oxadiazolonyl, [1,3,4]oxadiazinonyl, thiazolyl, thienyl, [1,2,3]triazinyl, [1,2,4]triazinyl, [1,3,5]triazinyl, [1,2,3]triazolyl, [1,2,4]triazolyl, pyridazinonyl, pyridonyl, and pyrimidinonyl. Preferred 5- to 6-membered heteroaryl rings are, for example, pyrimidinyl, pyridazinonyl, pyridinyl, and pyrazolyl. Each of the 5 to 6-membered heteroaryl rings is independently unsubstituted or substituted with substituents as described herein, for example as in the Examples or the Definitions.

Examples of 8- to 10-membered bicyclic heteroaryl rings suitable for $R_{6a}$ and $R_{6b}$ include, but are not limited to, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, and pyrrolopyrimidinyl. Preferred 8- to 10-membered bicyclic heteroaryl rings are, for example, benzothiazolyl. Each of the 8- to 10-membered bicyclic heteroaryl rings is independently unsubstituted or substituted with substituents as described herein, for example as in the Examples or the Definitions.

Examples of 4- to 8-membered heterocyclic ring suitable for $R_{6a}$ and $R_{6b}$ include, but are not limited to, azepanyl, azetidinyl, aziridinyl, azocanyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, and tetrahydropyranyl. Each of the heterocyclic ring is independently unsubstituted or substituted with substituents as described herein, for example as in the Examples or the Definitions.

In one preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 5- or 6-membered heteroaryl ring; and $R_2$, $R_3$, $R_{3a}$, $R_{3b}$, $R_4$, $R_5$, L, and n are as otherwise described In another preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 8- to 10-membered bicyclic heteroaryl ring; and $R_2$, $R_3$, $R_{3a}$, $R_{3b}$, $R_4$, $R_5$, L, and n are as otherwise described herein.

In another preferred embodiment, the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 4- to 8-membered heterocyclic ring; and $R_2$, $R_3$, $R_{3a}$, $R_{3b}$, $R_4$, $R_5$, L, and n are as otherwise described herein.

Each of $R_3$, $R_{3a}$, and $R_{3b}$ are independently selected from hydrogen, alkyl, alkoxy, halogen, cyano, and thioalkoxy. Preferably, $R_3$, $R_{3a}$, and $R_{3b}$ are hydrogen, or, one of $R_3$, $R_{3a}$, and $R_{3b}$ is halogen and the others are hydrogen. The preferred halogen is fluorine.

$R_4$ and $R_5$ are each independently selected from the group consisting of alkyl, fluoroalkyl, hydroxyalkyl, alkoxyalkyl, and cycloalkyl. Alternatively, $R_4$ and $R_5$ taken together with the nitrogen atom to which each is attached form a non-aromatic ring of the formula:

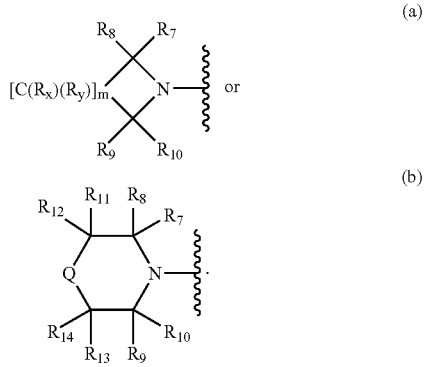

$R_7$, $R_8$, $R_9$, and $R_{10}$ are each independently selected from hydrogen, hydroxyalkyl, fluoroalkyl, cycloalkyl, and alkyl.

$R_x$ and $R_y$ at each occurrence are independently selected from the group consisting of hydrogen, hydroxy, alkyl, alkoxy, alkylamino, fluoro, and dialkylamino.

Preferably, at least one carbon in a group of formula (a) is substituted, such that either one of $R_7$, $R_8$, $R_9$, or $R_{10}$, or one of $R_x$ and $R_y$, is other than hydrogen. The preferred substituents for $R_7$, $R_8$, $R_9$, or $R_{10}$, when substituted, are hydroxyalkyl, fluoroalkyl, or alkyl. The preferred alkyl group is more particularly, methyl. The preferred substituents for $R_x$ or $R_y$, when substituted, are alkyl, fluoro, or hydroxy.

Groups of formula (a) are preferred for $R_4$ and $R_5$ when taken together to form a non-aromatic ring. The preferred group for $R_4$ and $R_5$ when taken together with the nitrogen atom to which each is attached to form a group of formula (a) is (2R)-methylpyrrolidine or (2S)-methylpyrrolidine.

$R_{11}$, $R_{12}$, $R_{13}$, and $R_{14}$ are each independently selected from hydrogen, hydroxyalkyl, alkyl, and fluoroalkyl. Preferably, at least three substituents selected from $R_{11}$, $R_{12}$, $R_{13}$, and $R_{14}$ are hydrogen.

Q is selected from O and S. The preferred atom for Q is oxygen.

The preferred group for $R_4$ and $R_5$ when taken together with the nitrogen atom to which each is attached to form a group of formula (b) is morpholinyl.

The variable m is an integer from 1 to 5.

L is —$[C(R_{16})(R_{17})]_k$, wherein $R_{16}$ and $R_{17}$ at each occurrence are independently selected from hydrogen and alkyl, and k is 0, 1, or 2. Preferably, k is 0 or 1.

The variable n is 0 or 1. Preferably, n is 0.

One embodiment of compounds of the invention are those of formula (II):

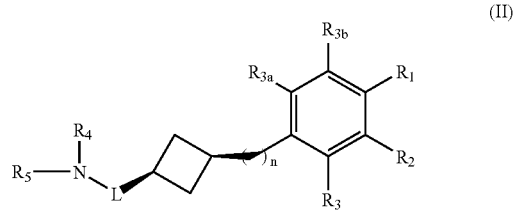

wherein L, n, $R_1$, $R_2$, $R_3$, $R_{3a}$, $R_{3b}$, $R_4$, and $R_5$ are as previously described.

In one preferred embodiment of compounds of the invention of formula (II), the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 5- or 6-membered heteroaryl ring; $R_4$ and $R_5$, when taken together with the nitrogen atom to which each is attached, form a 4- to 8-membered non-aromatic ring represented by formula (a), and $R_2$, $R_3$, $R_{3a}$, $R_{3b}$, L, and n are as previously described.

Another embodiment of compounds of the invention are those of formula (III):

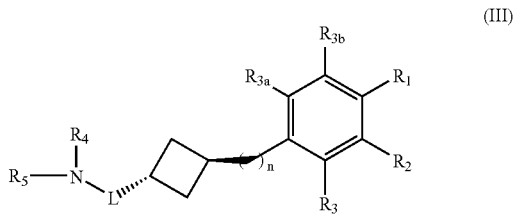

wherein L, n, $R_1$, $R_2$, $R_3$, $R_{3a}$, $R_{3b}$, $R_4$, and $R_5$ are as previously described.

In one preferred embodiment of compounds of the invention of formula (III), the group $R_1$ is -$L_2$-$R_{6a}$-$L_3$-$R_{6b}$, wherein $L_2$ is a bond; $R_{6b}$ is hydrogen; $L_3$ is a bond; $R_{6a}$ is selected from a 5- or 6-membered heteroaryl ring; $R_4$ and $R_5$ when taken together with the nitrogen atom to which each is attached to form a 4- to 8-membered non-aromatic ring represented by formula (a), and $R_2$, $R_3$, $R_{3a}$, $R_{3b}$, L, and n are as previously described.

Specific examples of compounds contemplated as within the scope of the invention include, but are not limited to, the following:

4'-{3-[(2R)-2-methyl-pyrrolidin-1-yl]-trans-cyclobutyl}-biphenyl-4-carbonitrile;
4'-{3[(2R)-2-methyl-pyrrolidin-1-yl]-cis-cyclobutyl}-biphenyl-4-carbonitrile;
4'-[3-(2-methyl-pyrrolidin-1-yl)-cis-cyclobutyl]-biphenyl-4-carbonitrile;
4'-[3-(2-methyl-pyrrolidin-1-yl)-trans-cyclobutyl]-biphenyl-4-carbonitrile;
5-{4-[3-({2R}-2-methyl-pyrrolidin-1-yl)-cis-cyclobutyl]-phenyl}-pyrimidine;
2,6-difluoro-3-{4-[3-({2R})-2-methyl-pyrrolidin-1-yl)-cis-cyclobutyl]-phenyl}-pyridine;
2,6-difluoro-3-{4-[3-({2R}-2-methyl-pyrrolidin-1-yl)-trans-cyclobutyl]-phenyl}-pyridine;
2,6-dimethyl-3-{4-[3-({2R}-2-methyl-pyrrolidin-1-yl)-trans-cyclobutyl]-phenyl}-pyridine;
2,6-dichloro-3-{4-[3-({2R}-2-methyl-pyrrolidin-1-yl)-trans-cyclobutyl]-phenyl}-pyridine;
4'-{3-[(2S)-2-methyl-pyrrolidin-1-yl]-cis-cyclobutyl}-biphenyl-4-carbonitrile;
5-{4-[3-({2R}-2-methyl-pyrrolidin-1-yl)-trans-cyclobutyl]-phenyl}-pyrimidine;
2-{4-[3-({2R})-2-methyl-pyrrolidin-1-yl)-trans-cyclobutyl]-phenyl}-2H-pyridazin-3-one;
4'-{3-[(2S)-2-methyl-pyrrolidin-1-yl]-trans-cyclobutyl}-biphenyl-4-carbonitrile;
5-{4-[3-({2S}-2-methyl-pyrrolidin-1-yl)-trans-cyclobutyl]-phenyl}-pyrimidine;
2,4-dimethoxy-5-{4-[3-({2S}-2-methyl-pyrrolidin-1-yl)-trans-cyclobutyl]-phenyl}-pyrimidine;
2-methoxy-5-{4-[3-({2R}-2-methyl-pyrrolidin-1-yl)-trans-cyclobutyl]-phenyl}-pyrimidine;
2,4-dimethoxy-5-{4-[3-({2R}-2-methyl-pyrrolidin-1-yl)-trans-cyclobutyl]-phenyl}-pyrimidine;
5-{4-[3-({2R}-2-methyl-pyrrolidin-1-yl)-trans-cyclobutyl]-phenyl}-nicotinonitrile;
2-methyl-5-{4-[3-({2R}-2-methyl-pyrrolidin-1-yl)-trans-cyclobutyl]-phenyl}-benzothiazole;
2-methyl-5-{4-[3-({2R}-2-methyl-pyrrolidin-1-yl)-trans-cyclobutyl]-phenyl}-pyridine;
1,3,5-trimethyl-4-{4-[3-(2-methyl-pyrrolidin-1-yl)-trans-cyclobutyl]-phenyl}-1H-pyrazole;
5-{2-fluoro-4-[3-({2R}-2-methyl-pyrrolidin-1-yl)-trans-cyclobutyl]-phenyl}-pyrimidine;
4'-{3-[(2R)-2-methyl-pyrrolidin-1-ylmethyl]-cis-cyclobutyl}-biphenyl-4-carbonitrile;
4'-{3-[(2R)-2-methyl-pyrrolidin-1-ylmethyl]-trans-cyclobutyl}-biphenyl-4-carbonitrile;
4'-{3-[(2S)-2-methyl-pyrrolidin-1-ylmethyl]-cis-cyclobutyl}-biphenyl-4-carbonitrile;
2,6-difluoro-3-{4-[3-(2-methyl-pyrrolidin-1-ylmethyl)-cis-cyclobutyl]-phenyl}-pyridine;
5-{4-[3-(2-methyl-pyrrolidin-1-ylmethyl)-cis-cyclobutyl]-phenyl}-pyrimidine;
4'-[3-(2-methyl-pyrrolidin-1-ylmethyl)-cis-cyclobutyl]-biphenyl-4-carbonitrile;
1,3,5-trimethyl-4-{4-[3-({2R}-2-methyl-pyrrolidin-1-ylmethyl)-cis-cyclobutyl]-phenyl}-1H-pyrazole;
2-{4-[3-({2R}-2-methyl-pyrrolidin-1-ylmethyl)-cis-cyclobutyl]-phenyl}-2H-pyridazin-3-one;
2-methoxy-5-{4-[3-({2R}-2-methyl-pyrrolidin-1-ylmethyl)-cis-cyclobutyl]-phenyl}-pyrimidine;
2,4-dimethoxy-5-{4-[3-({2R}-2-methyl-pyrrolidin-1-ylmethyl)-cis-cyclobutyl]-phenyl}-pyrimidine; and
4'-{3-[(2R)-2-methyl-pyrrolidin-1-yl]-cis-cyclobutylmethyl}-biphenyl-4-carbonitrile.

A preferred compound is 2-methoxy-5-{4-[3-({2R}-2-methyl-pyrrolidin-1-yl)-trans-cyclobutyl]-phenyl}-pyrimidine.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Ac for acetyl; atm for atmosphere(s); BINAP for 2,2'-bis(diphenylphosphino)-1,1'-binaphthyl; Boc for butyloxycarbonyl; Bu for butyl; DCM for dichloromethane; DMAP for 4-(N,N-dimethylamino)pyridine; DMF for N,N-dimethylformamide; DMSO for dimethylsulfoxide; dppf for 1,1'-bis(diphenylphosphino)ferrocene; EDTA for ethylenediaminetetraacetic acid; Et for ethyl; EtOH for ethanol; EtOAc for ethyl acetate; HPLC for high pressure liquid chromatography; IPA for isopropyl alcohol; IPAC or IPAc for isopropyl acetate; LDA for lithium diisopropylamide; NBS for N-bromosuccinimide; NIS for N-iodosuccinimide; Me for methyl; MeOH for methanol; Ms for methanesulfonyl; MTBE for tert-butyl methyl ether; Pd for palladium; tBu for tert-butyl; TEA for triethylamine; TFA for trifluoroacetic acid; THF for tetrahydrofuran; and Ts for para-toluenesulfonyl; rt for "room temperature" or ambient temperature suitably ranging 15-40° C.

The compounds of this invention can be prepared by a variety of synthetic procedures. Representative procedures are shown in, but are not limited to, Schemes 1-10.
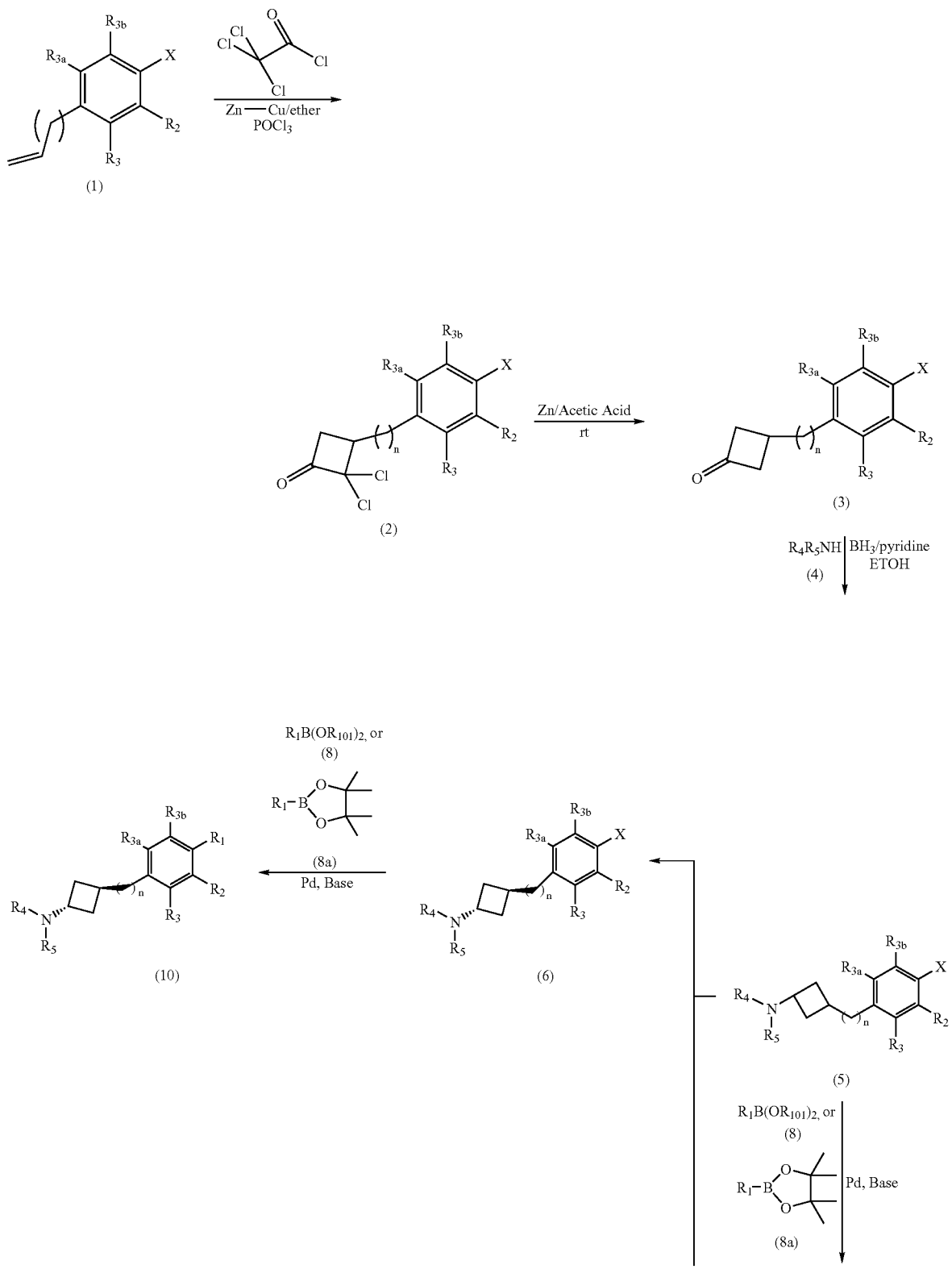
Scheme 1

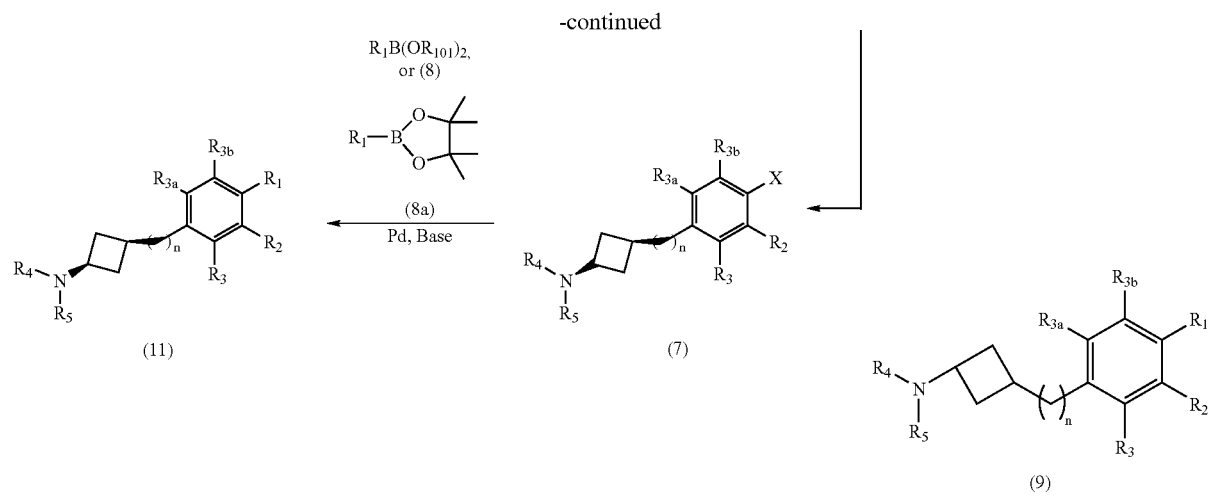

Compounds of formulas (9), (10), and (11), wherein n, $R_3$, $R_{3a}$, $R_{3b}$, $R_4$, and $R_5$ are as defined in formula (I), $R_1$ is $-L_2-R_{6a}-L_3-R_{6b}$, and $R_2$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are defined in formula (I), can be prepared as described in Scheme 1. Alkenes of formula (1) wherein X is Cl, Br, I, or triflate, purchased or prepared using methodologies known to those of ordinary skill in the art, can be reacted with a ketene such as, but not limited to, dichloroketene generated in situ from trichloroacetyl chloride and activated Zn, to provide cyclobutanones of formula (2). References that describe this cycloaddition reaction and the subsequent reduction to form the cyclobutanones of formula (3), may be found in the following: L. R. Krepski et al., J. Org. Chem., 43:2879-1882 (1978); W. T. Brandy et al., J. Org. Chem., 32:3703-3705 (1967); R. R. Srivastava et al., J. Org. Chem., 64:8495-8500 (1999); T. D. Penning et al., J. Med. Chem., 43:721-735 (2000). Cyclobutanones of formula (2) can be reduced with a reducing agent, such as, but not limited to, Zn to provide cyclobutanones of formula (3). Cyclobutanones of formula (3) can be treated with a reducing agent such as, but not limited to, borane-pyridine complex, in the presence of an amine of formula (4), via a reaction known as reductive amination, to provide amines of formula (5). References that describe this methodology may be found in the following: M. D. Bomann et al., J. Org. Chem., 60:5995-5960(1995); A. E. Moormann et al., Synth. Commun., 23:789-795(1993); A. Pelter et al., J. Chem. Soc., PT I, 4:717-720(1984). Separation of products by, for example, using column chromatography provides trans-substituted cyclobutanes of formula (6) and cis-substituted cyclobutanes of formula (7).

Suzuki reaction can be used to convert compounds of formula (5) to compounds of formula (9) wherein n, $R_3$, $R_{3a}$, $R_{3b}$, $R_4$, and $R_5$ are as defined in formula (I), $R_2$ is hydrogen, alkyl, alkoxy, halogen, cyano, or thioalkoxy, and $R_1$ is $-L_2-R_{6a}-L_3-R_{6b}$, wherein $L_2$ is a bond and $R_{6a}$, and $L_3$ and $R_{6b}$ are as defined in formula (I). In such a Suzuki reaction, amines of formula (5), wherein X is triflate, I, Br, or Cl can be reacted with boronic acids or boronic esters of formula (8) wherein $R_{101}$ is hydrogen or alkyl, a metal catalyst such as, but not limited to, palladium diacetate or Pd(PPh$_3$)$_4$, optionally with a Pd ligand added such as 2-(dicyclohexylphosphino)biphenyl or tris(2-furyl)phosphine, and a base such as, but not limited to, aqueous 0.2 M K$_3$PO$_4$ or sodium carbonate.

Alternatively, pinacol borane reagents such as, but not limited to, those represented by formula (8a) can be used in place of boronic acids or esters of formula (8) in the Suzuki reaction. References that describe the Suzuki reaction methodology may be found in the following: N. Miyaura et al., Chem. Rev. 95:2457(1995) and references cited in the article.

Likewise, amines of formulas (6) or (7) can be subjected to the Suzuki reaction conditions as outlined above to provide the corresponding amines of formula (10) or (11) wherein n, $R_3$, $R_{3a}$, $R_{3b}$, $R_4$, and $R_5$ are as defined in formula (I), $R_2$ is hydrogen, alkyl, alkoxy, halogen, cyano or thioalkoxy, and $R_1$ is $-L_2-R_{6a}-L_3-R_{6b}$, wherein $L_2$ is a bond and $R_{6a}$, and $L_3$ and $R_{6b}$ are as defined in formula (I).

There are many aryl, heteroaryl, and heterocyclic boronic acids and boronic acid esters that are available commercially or that can be prepared as described in the scientific literature of synthetic organic chemistry. Examples of boronic acid and boronic acid ester reagents for the synthesis of compounds of formula (I) are provided, but not limited to, reagents shown in Table 1, below, and the following description.

TABLE 1

Examples of Boronic Acid and Boronic Acid Ester Reagents

| Boronic Acid or Boronic Acid Ester | Commercial Source, Chemical Abstracts Number (CAS #), or Literature Reference |
|---|---|
| 2-pyrimidinone-5-boronic acid | CAS #373384-19-1 |
| 2-methoxypyrimidine-5-boronic acid | Frontier Scientific, Inc., Logan, UT, USA |

TABLE 1-continued

Examples of Boronic Acid and Boronic Acid Ester Reagents

| Boronic Acid or Boronic Acid Ester | Commercial Source, Chemical Abstracts Number (CAS #), or Literature Reference |
|---|---|
| 1H-pyrimidine-2,4-dione-5-boranic acid | Specs, Fleminglaan, the Netherlands CAS #70523-22-7; Schinazi, Raymond F.; Prusoff, William H., Synthesis of 5-(dihydroxyboryl)-2'-deoxyuridine and related boron-containing pyrimidines, Journal of Organic Chemistry (1985), 50(6), 841-7. |
| pyridine-3-boronic acid | CAS #1692-25-7, Frontier Scientific, Inc., Logan, UT, USA |
| 2,4-dimethoxypyrimidine-5-boronic acid | CAS #89641-18-9, Frontier Scientific, Inc., Logan, UT, USA |
| 2-methoxy-5-pyridine boronic acid | Digital Specialty Chemicals, Dublin, NH; CAS #163105-89-3; New shelf-stable halo- and alkoxy-substituted pyridylboronic acids and their Suzuki cross-coupling reactions to yield heteroarylpyridines, Parry, Paul R.; Bryce, Martin R.; Tarbit, Brian, Department of Chemistry, Synthesis (2003), (7), 1035-1038; Functionalized Pyridylboronic Acids and Their Suzuki Cross-Coupling Reactions To Yield Novel Heteroarylpyridines, Parry, Paul R.; Wang, Changsheng; Batsanov, Andrei S.; Bryce, Martin R.; Tarbit, Brian, Journal of Organic Chemistry (2002), 67(21), 7541-7543. |
| pyrimidine-5-boronic acid | CAS #109299-78-7, S. Gronowitz, et al., "On the synthesis of various thienyl- and selenienylpyrimidines", Chem. Scr. 26(2): 305-309 (1986). |
| pyrimidine-5-boronic acid, pinacol ester | Umemoto, et al., Angew. Chem. Int. Ed. 40(14): 2620-2622 (2001). |
| 2-methylpyridine-5-boronic acidhydrate | SYNCHEM OHG Heinrich-Plett-Strassse 40; Kassel, D-34132; Germany; CAS #659742-21-9 |
| 2H-Pyran, 3,6-dihydro-4-(4,4,5,5-tetramethyl-1,3,2-dioxaborolan-2-yl) | CAS # 287944-16-5; Murata, Miki; Oyama, Takashi; Watanabe, Shinji; Masuda, Yuzuru, Synthesis of alkenylboronates via palladium-catalyzed borylation of alkenyl triflates (or iodides) with pinacolborane. Synthesis(2000), (6), 778-780. |
| 1(2H)-Pyridinecarboxylic acid, 3,6-dihydro-4-(4,4,5,5-tetramethyl-1,3,2-dioxaborolan-2-yl)-, 1,1-dimethylethyl ester | CAS # 286961-14-6; A versatile synthesis of 4-aryltetrahydropyridines via palladium mediated Suzuki cross-coupling with cyclic vinyl boronates, Eastwood, Paul R., Discovery Chemistry, Aventis Pharma, Essex, UK., Tetrahedron Letters (2000), 41(19), 3705-3708. |
| (5-cyano-3-pyridinyl)-boronic acid | CAS # 497147-93-0; Chemstep Institut du PIN - University Bordeaux 1 351 cours de la liberation Talence Cedex, 33450 France |

Boronic acids or boronic acid esters of formula (8), (8a), (18) and (18a) can be prepared from corresponding halides or triflates via either (1) metal exchange with an organo lithium agent followed with addition of alkyl borate or pinacolborate or (2) cross coupling with a reagent such as, but not limited to, bis(pinacolato)diboron (CAS #73183-34-3). References that describe the first methodology may be found in the following: B. T. O'Neill, et al., Organic Letters, 2:4201 (2000); M. D. Sindkhedkar, et al., Tetrahedron, 57:2991 (2001); W. C. Black, et al., J. Med. Chem., 42:1274 (1999); R. L. Letsinger et al., J. Amer. Chem. Soc., 81:498-501 (1959); and F. I. Carroll et al., J. Med. Chem., 2229-2237 (2001). References that describe the second methodology may be found in the following: T. Ishiyama et al., Tetrahedron, 57:9813-9816 (2001); T. Ishiyama et al., J. Org. Chem., 60:7508-7510 (1995); and Takagi et al., Tetrahedron Letters, 43:5649-5651 (2002).

Another method for preparation of boronic acids and boronic acid esters is the reaction described in O. Baudoin, et al., J. Org. Chem., 65:9268-9271 (2000), in which aryl and heteroaryl halides or triflates are reacted with a dialkyloxyborane such as pinacolborane, in the presence of triethylamine and palladium(II) acetate in dioxane.

Alternatively, utilizing other coupling methods such as Stille coupling, compounds of formulas (9), (10), and (11) wherein n, $R_3$, $R_{3a}$, $R_{3b}$, $R_4$, and $R_5$ are as defined in formula (I), $R_2$ is hydrogen, alkyl, alkoxy, halogen, cyano or thioalkoxy, and $R_1$ is -$L_2$-$R_{6a}$-$L_3$-$R_{6b}$, wherein $L_2$ is a bond and $R_{6a}$, $L_3$, and $R_{6b}$ are as defined in formula (I), can be prepared from amines of formulas (5), (6), and (7) respectively, by treatment with organostannanes of formula $(R_{102})_3SnR_1$ wherein $R_{102}$ is alkyl or aryl, in the presence of a palladium source such as tris(dibenzylidineacetone)dipalladium (CAS # 52409-22-0) or palladium diacetate, and a ligand such as tri(2-furyl)phosphine (CAS # 5518-52-5) or triphenylarsine. The reaction is generally performed in a solvent such as DMF at a temperature from about 25° C. to about 150° C. Such methods are described, for instance, in J. K. Stille Angew. Chem. Int. Ed. 25:508(1986) and T. N. Mitchell, Synthesis, 803(1992).

While many stannanes are commercially available or described in the literature that support the Stille coupling reaction where compounds of formulas (5), (6), and (7) can be transformed to compounds of formulas (9), (10), and (11), respectively, it is also possible to prepare new stannanes from arylhalides, aryltriflates, heteroarylhalides, and heteroaryltriflates by reaction with hexa-alkyl distannanes of formula $((R_{102})_3Sn)_2$ wherein $R_{102}$ is alkyl or aryl, in the presence of a palladium source like $Pd(Ph_3P)_4$. Example of hexa-alkyl distannanes include, but not limited to, hexamethyldistannane (CAS # 661-69-8). Such methods are described, for instance in Krische, et. al., Helvetica Chimica Acta 81(11): 1909-1920 (1998), and in Benaglia, et al., Tetrahedron Letters 38:4737-4740 (1997). These reagents can be reacted with (5), (6), and (7) to afford compounds of formulas (9), (10), and (11) respectively as described under Stille conditions, or for example under the conditions reported by A. F. Littke et al., J. of Amer. Chem. Soc. 124:6343-6348 (2002).

Compounds of formulas (9), (10), and (11) wherein n, $R_3$, $R_{3a}$, $R_{3b}$, $R_4$, and $R_5$ are as defined in formula (I), $R_2$ is hydrogen, alkyl, alkoxy, halogen, cyano or thioalkoxy, and $R_1$ is $-L_2-R_{6a}-L_3-R_{6b}$, wherein $L_3$ and $R_{6b}$ are as defined in formula (I), $L_2$ is a bond, and $R_{6a}$ is a nitrogen-containing heteroaryl or heterocyclic ring linked to the parent moiety through the nitrogen, can be prepared by heating compounds of formulas (5), (6), and (7) respectively, with heteroaryl or heterocyclic rings of formula $H-R_{6a}L_3R_{6b}$ wherein H is a hydrogen on the nitrogen atom, in the presence of a base such as, but not limited to, sodium t-butoxide or cesium carbonate, a metal catalyst such as, but not limited to copper metal or CuI, palladium diacetate, and optionally with a ligand such as, but not limited to, BINAP or tri-tertbutylphosphine. The reaction can be conducted in a solvent such as, but not limited to, dioxane, toluene or pyridine. References that describe these methods may be found in the following: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174(2000); F. Y. Kwong et al., Org. Lett., 4:581-584(2002); A. Klapars et al., J. Amer. Chem. Soc., 123:7727-7729 (2001); B. H. Yang et al., J. Organomet. Chem., 576:125-146 (1999); and A. Kiyomori et al., Tet. Lett., 40:2657-2640 (1999).

Compounds of formulas (9), (10), and (11) wherein n, $R_3$, $R_{3a}$, $R_{3b}$, $R_4$, and $R_5$ are as defined in formula (I), $R_2$ is hydrogen, alkyl, alkoxy, halogen, cyano, or thioalkoxy, and $R_1$ is $-L_2-R_{6a}-L_3-R_{6b}$, wherein $L_2$ is —NH— or —N(alkyl)-, and $R_{6a}$, $R_{6b}$, and $L_3$ are as defined for a compound of formula (I) can be prepared by heating compounds of formula (5), (6), and (7) respectively, with a compound of formula $H_2N-R_{6a}-L_3-R_{6b}$ or $HN(alkyl)-R_{6a}-L_3-R_{6b}$ with a base such as, but not limited to, sodium t-butoxide or cesium carbonate in the presence of a metal catalyst such as, but not limited to, copper metal or CuI, palladium diacetate, and also optionally with a ligand such as, but not limited to, BINAP, or tri-tert-butylphosphine. The reaction can be performed in a solvent such as dioxane, toluene, or pyridine. References that describe these methodologies may be found in the following: J. Hartwig, et al., Angew. Chem. Int. Ed., 37:2046-2067 (1998); J. P. Wolfe et al., Acc. Chem. Res., 13:805-818 (1998); J. P. Wolfe et al., J. Org. Chem., 65:1158-1174 (2000); F. Y. Kwong et al., Org. Lett., 4:581-584(2002); and B. H. Yang et al., J. Organomet. Chem., 576:125-146 (1999).

Compounds of formulas (9), (10), and (11) wherein n, $R_3$, $R_{3a}$, $R_{3b}$, $R_4$ and $R_5$ are as defined in formula (I), $R_2$ is hydrogen, alkyl, alkoxy, halogen, cyano, or thioalkoxy, and $R_1$ is $L_2-R_{6a}-L_3-R_{6b}$, wherein $L_2$ is oxygen and $R_{6a}$, and $L_3$ and $R_{6b}$ are as defined in formula (I) can be prepared by heating compounds of formula (5), (6), and (7) respectively with a compound of formula $HOR_{6a}-L_3-R_{6b}$ using a base such as, but not limited to, sodium hydride in a solvent such as toluene or N,N-dimethylformamide, in the presence of a metal containing catalyst such as CuI or palladium diacetate. References that describe these methodologies may be found in the following: J. Hartwig et al., Angew. Chem. Int. Ed., 37:2046-2067 (1998); K. E. Torraca et al., J. Amer. Chem. Soc., 123: 10770-10771 (2001); S. Kuwabe et al., J. Amer. Chem. Soc., 123:12202-12206 (2001); K. E. Toracca et al., J. Am. Chem. Soc., 122:12907-12908 (2000); R. Olivera et al., Tet. Lett., 41:4353-4356 (2000); J.-F. Marcoux et al., J. Am. Chem. Soc., 119:10539-10540 (1997); A. Aranyos et al., J. Amer. Chem. Soc., 121:4369-4378 (1999); T. Satoh et al., Bull. Chem. Soc. Jpn., 71:2239-2246 (1998); J. F. Hartwig, Tetrahedron Lett., 38:2239-2246 (1997); M. Palucki et al., J. Amer. Chem. Soc., 119:3395-3396 (1997); N. Haga et al, J. Org. Chem., 61:735-745 (1996); R. Bates et al., J. Org. Chem., 47:4374-4376 (1982); T. Yamamoto et al., Can. J. Chem., 61:86-91 (1983); A. Aranyos et al., J. Amer. Chem. Soc., 121:4369-4378 (1999); and E. Baston et al., Synth. Commun., 28:2725-2730 (1998).

Compounds of formulas (9), (10), and (11) wherein n, $R_3$, $R_{3a}$, $R_{3b}$, $R_4$ and $R_5$ are as defined in formula (I), $R_2$ is hydrogen, alkyl, alkoxy, halogen, cyano, or thioalkoxy, and $R_1$ is $L_2-R_{6a}-L_3-R_{6b}$, wherein $L_2$ is sulfur and $R_{6a}$, and $L_3$ and $R_{6b}$ are as defined for a compound of formula (I) can be prepared by heating compounds of formula (5), (6), and (7) respectively with a compound of formula $HSR_{6a}-L_3-R_{6b}$ in the presence of a base, and with or without a metal catalyst such as CuI or palladium diacetate, in a solvent such as dimethylformamide or toluene. References that describe these methodologies may be found in the following: G. Y. Li et al., J. Org. Chem., 66:8677-8681 (2001); Y. Wang et al., Bioorg. Med. Chem. Lett., 11:891-894 (2001); G. Liu et al., J. Med. Chem., 44:1202-1210 (2001); G. Y. Li et al., Angew. Chem. Int. Ed., 40:1513-1516 (2001); U. Schopfer et al., Tetrahedron, 57:3069-3074 (2001); and C. Palomo et al., Tet. Lett., 41:1283-1286 (2000); A. Pelter et al., Tet. Lett., 42:8391-8394 (2001); W. Lee et al., J. Org. Chem., 66:474-480 (2001); and A. Toshimitsu et al., Het. Chem., 12:392-397 (2001).

Scheme 2
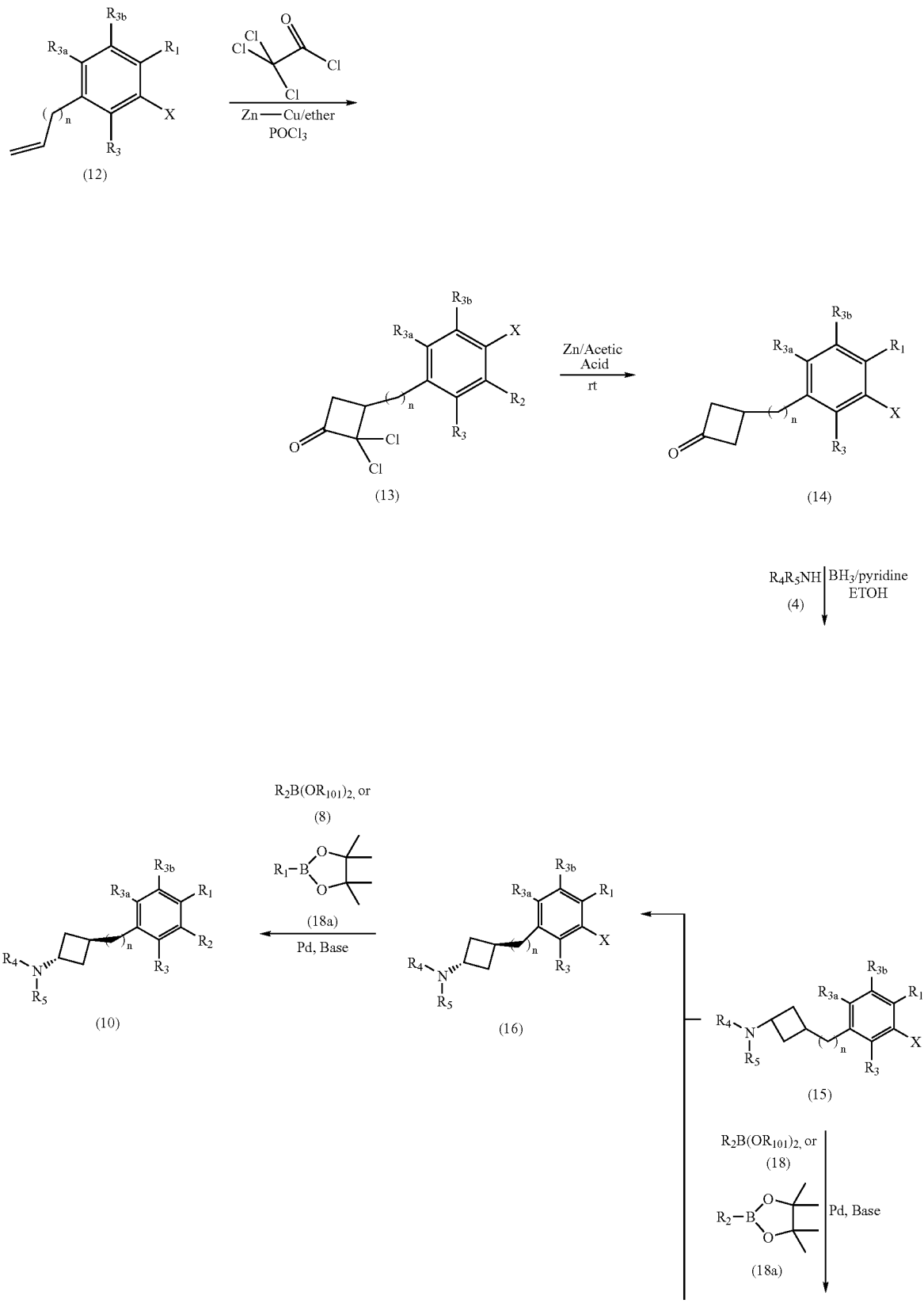

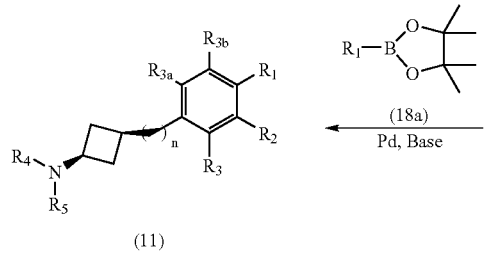
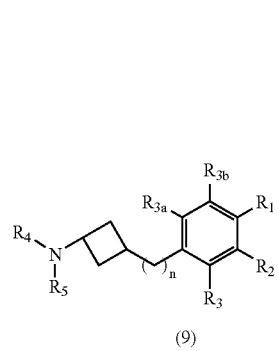
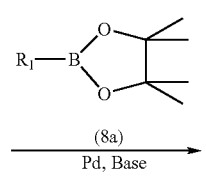
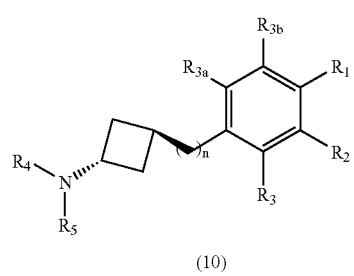

Similarly, compounds of formulas (9), (10), and (11) wherein n, $R_3$, $R_{3a}$, $R_{3b}$, $R_4$ and $R_5$ are as defined in formula (I), $R_1$ is hydrogen, alkyl, alkoxy, halogen, cyano, or thioalkoxy, and $R_2$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 2, from compounds of formula (12) wherein X is Cl, Br, I, or triflate, using the reaction conditions that are outlined in Scheme 1, except for substituting boronic acid or esters of formula (18) for (8) and pinacol borane reagents of formula (18a) for (8a) for the Suzuki reactions, and except for substituting organostannes of formula $(R_{102})_3SnR_2$ for $(R_{102})_3SnR_1$ for Stille coupling. References that describe the Suzuki reaction methodology may be found in the following: N. Miyaura et al., Chem. Rev. 95:2457(1995) and references cited in the article.

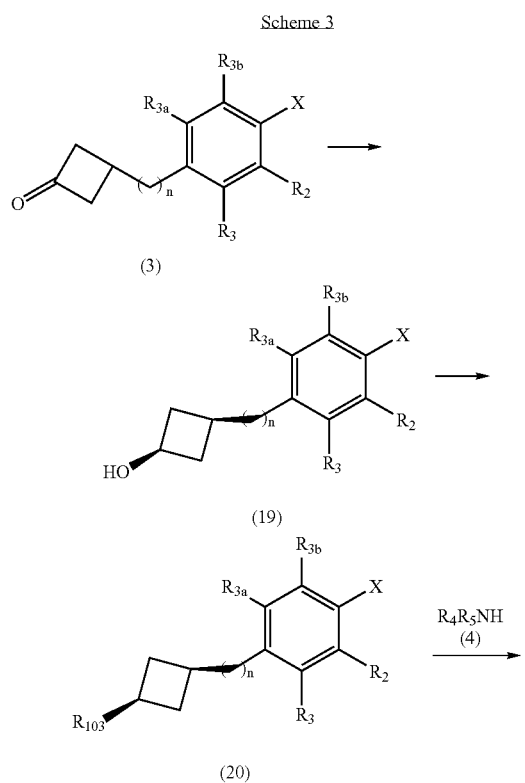

Alternatively, trans-substituted cyclobutyl amines of formula (10), wherein n, $R_3$, $R_{3a}$, $R_{3b}$, $R_4$, and $R_5$ are as defined in formula (I); $R_1$ is -$L_2$-$R_{6a}$-$L_3$-$R_{6b}$, and $R_2$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are as defined in formula (I), can be prepared as described in Scheme 3. Cyclobutanones of formula (3) can be treated with a reducing agent such as, but not limited to, sodium borohydride, lithium selectride, or lithium aluminium hydride to provide cis substituted cyclobutyl alcohols of formula (19). Reference for this method may be found in: E. Dehmlow et al., Chemische Berichte, 126:2759-2763(1993). Alcohols of formula (19) can be treated with an agent such as, but not limited to, triflate anhydride, tosyl chloride, or mesyl chloride in the presence of a base such as, but not limited to, potassium carbonate, to provide compounds of formula (20) wherein $R_{103}$ is triflate, tosylate, or mesylate respectively. Compounds of formula (20) can be treated with an amine of formula (4), optionally in the presence of a base such as, but not limited to, potassium carbonate or sodium carbonate, to provide trans substituted cyclobutyl amines of formula (6).

Compounds of formula (6) can be converted to amines of formula (10) using the reaction conditions described in Scheme 1.

Scheme 4

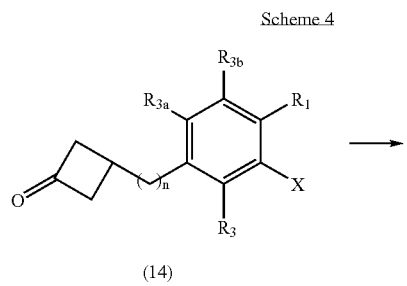

(14)

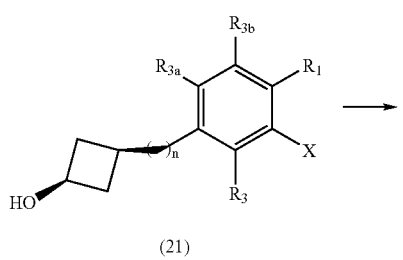

(21)

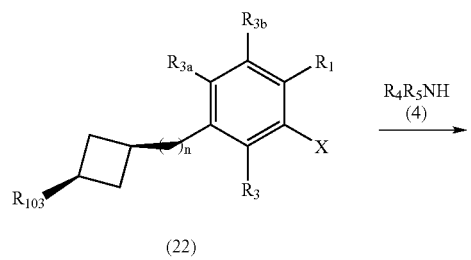

(22)

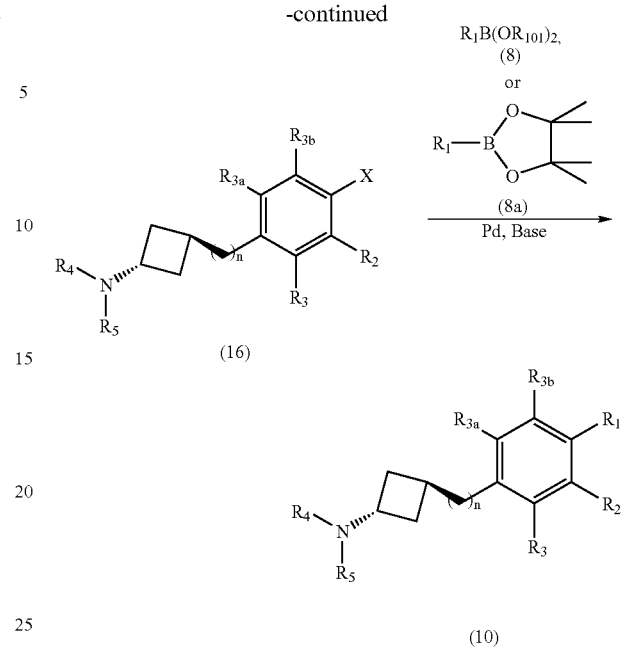

Similarly, trans-substituted cyclobutyl amines of formula (10), wherein n, $R_3$, $R_{3a}$, $R_{3b}$, $R_4$, and $R_5$ are as defined in formula (I); $R_2$ is $-L_2-R_{6a}-L_3-R_{6b}$, and $R_1$ is hydrogen, alkyl, alkoxy, halogen, cyano, or thioalkoxy, wherein $L_2$ is a bond, —N(H), —N(alkyl), —O—, or —S—, and $R_{6a}$, $L_3$, and $R_{6b}$ are as defined in formula (I), can be prepared as described in Scheme 4. Cyclobutanones of formula (14) wherein X is Br, Cl, or I, can be converted to amines of formula (10) using the reaction conditions as described in Scheme 3, except for substituting boronic acid or esters of formula (18) for (8) and pinacol borane reagents of formula (18a) for (8a) for the Suzuki reactions, and except for substituting organostannes of formula $(R_{102})_3SnR_2$ for $(R_{102})_3SnR_1$ for Stille coupling.

Scheme 5

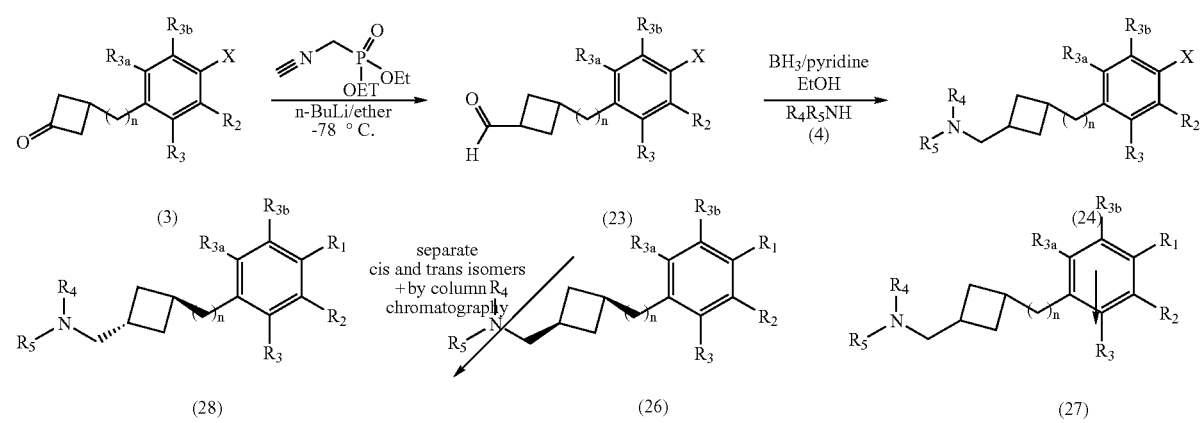

-continued

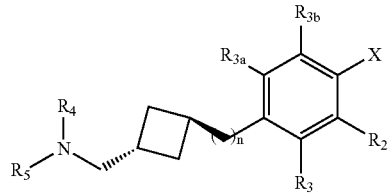

(28)

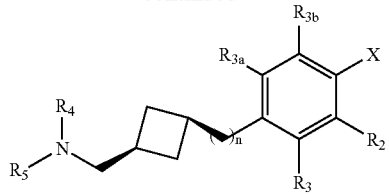

(29)

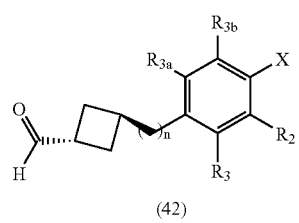

(42)

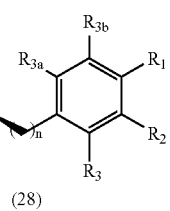

(8a)
Pd, Base

→ (28)

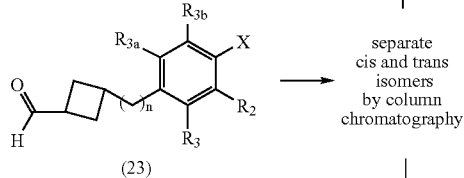

(23)

separate
cis and trans
isomers
by column
chromatography

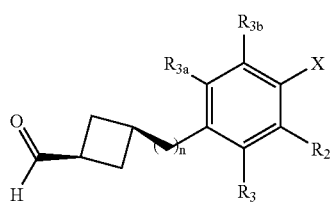

(43)

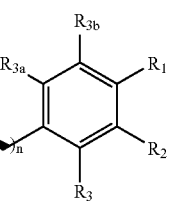

(8a)
Pd, Base

→ (29)

Compounds of formulas (27), (28), and (29), wherein n, $R_3$, $R_{3a}$, $R_{3b}$, $R_4$, and $R_5$ are as defined in formula (I); $R_2$ is hydrogen, alkyl, alkoxy, halogen, cyano, or thioalkoxy; and $R_1$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 5. Cyclobutanones of formula (3), wherein X is Br, Cl, or I, can be treated with the anion of diethyl isocyanomethylphosphonate generated with an organo lithium reagent such as, but not limited to, n-butyllithium, sec-butyllithium, or tert-butyllithium to provide aldehydes of formula (23). Aldehydes of formula (23) can be treated with a reducing agent such as, but not limited to, borane-pyridine complex or sodium triacetoxyborohydride, in the presence of an amine of formula (4) via a reaction known as reductive amination to provide amines of formula (24). The trans and cis amines of formulas (25) and (26) may be separated or purified by, for-instance, using column chromatography. The amines of formulas (24), (25), and (26) can be processed as described in Scheme 1 to provide compounds of formulas (27), (28), and (29) respectively.

Alternatively, compounds of formula (28) and (29), wherein n, $R_3$, $R_{3a}$, $R_{3b}$, $R_4$, and $R_5$ are as defined in formula (I), $R_2$ is hydrogen, alkyl, alkoxy, halogen, cyano, or thioalkoxy, and $R_1$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can also be prepared from the aldehyde of formula (23) wherein the aldehyde is first purified to obtain separately, the cis isomer of formula (43) and the trans isomer of formula (42) by use of column chromatography. The trans aldehyde (42) can be converted to the trans amine of (25) by the process of reductive amination as described above, followed by conversion to compounds of formula (28) by use of the reaction conditions previously described in Scheme 1 for the conversion of (6) to (10) and (7) to (11). Similarly, the cis aldehyde (43) can be converted to the cis amines of formula (29).

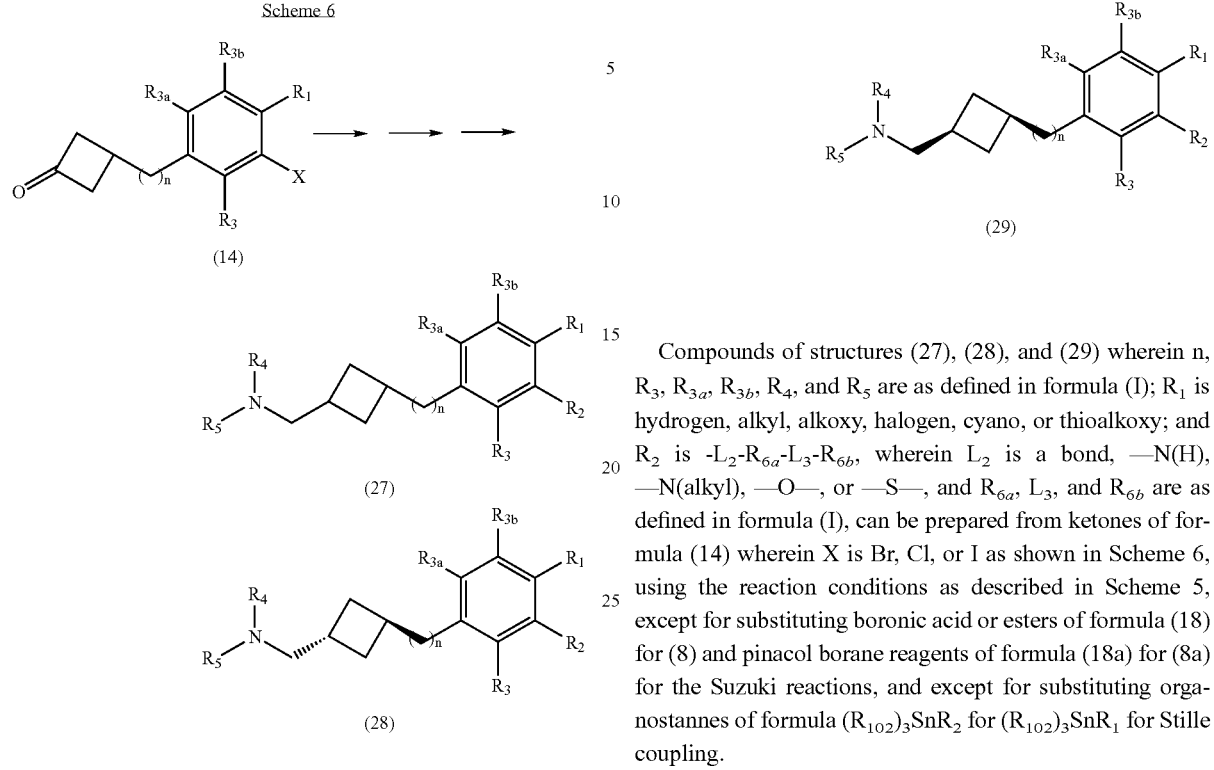

Compounds of structures (27), (28), and (29) wherein n, $R_3$, $R_{3a}$, $R_{3b}$, $R_4$, and $R_5$ are as defined in formula (I); $R_1$ is hydrogen, alkyl, alkoxy, halogen, cyano, or thioalkoxy; and $R_2$ is $-L_2-R_{6a}-L_3-R_{6b}$, wherein $L_2$ is a bond, —N(H), —N(alkyl), —O—, or —S—, and $R_{6a}$, $L_3$, and $R_{6b}$ are as defined in formula (I), can be prepared from ketones of formula (14) wherein X is Br, Cl, or I as shown in Scheme 6, using the reaction conditions as described in Scheme 5, except for substituting boronic acid or esters of formula (18) for (8) and pinacol borane reagents of formula (18a) for (8a) for the Suzuki reactions, and except for substituting organostannes of formula $(R_{102})_3SnR_2$ for $(R_{102})_3SnR_1$ for Stille coupling.

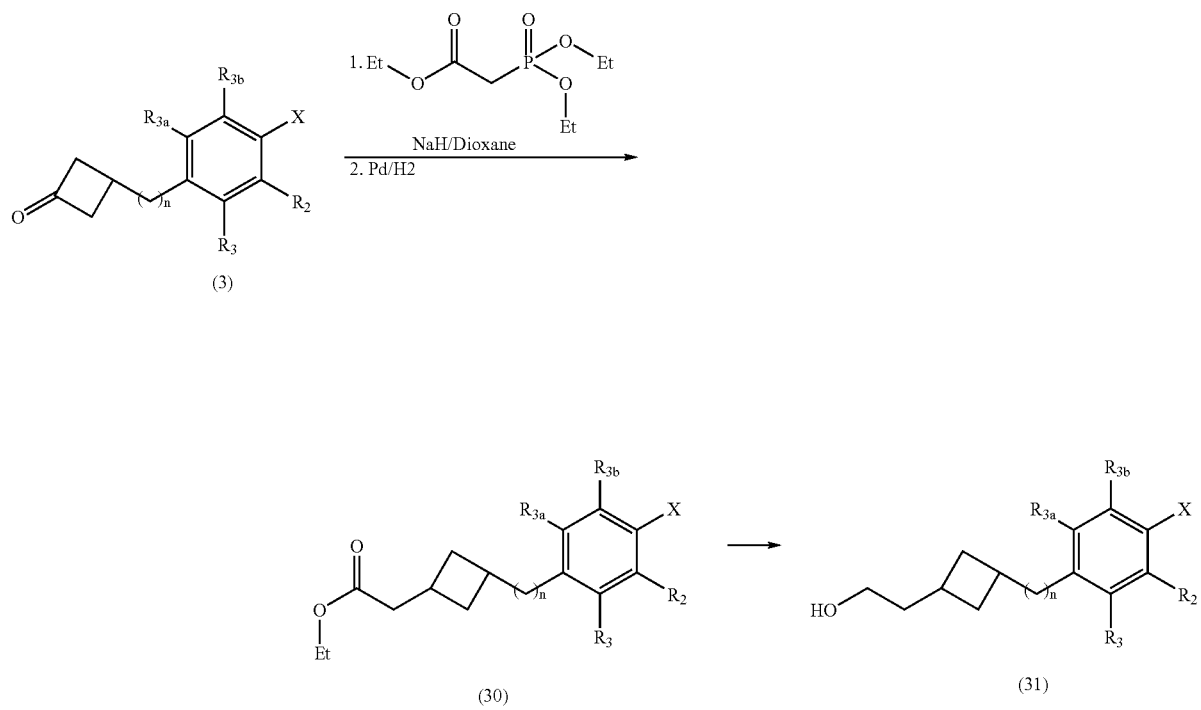

-continued

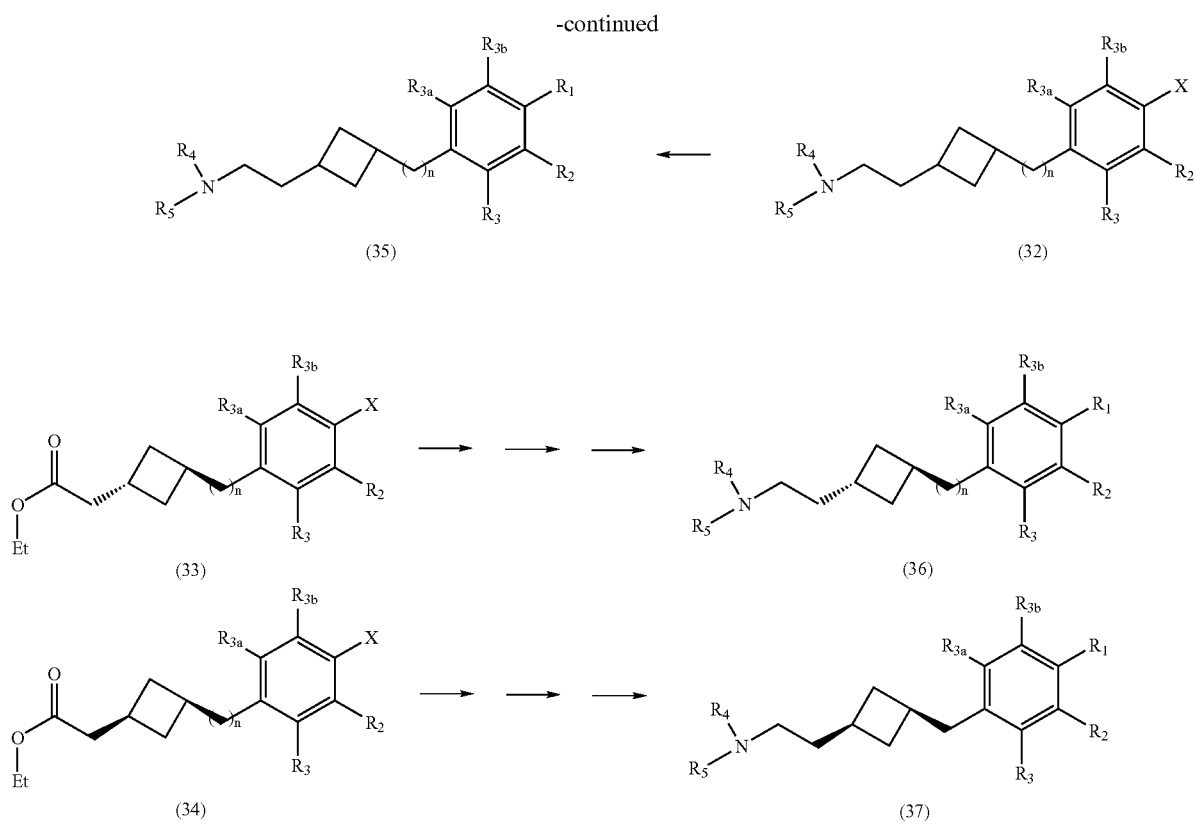

Compounds of formulas (35), (36), and (37), wherein n, $R_3$, $R_{3a}$, $R_{3b}$, $R_4$, and $R_5$ are as defined in formula (I); $R_2$ is hydrogen, alkyl, alkoxy, halogen, cyano, or thioalkoxy; and $R_1$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 7. Cyclobutanones of formula (3), wherein X is Br, Cl, or I, can be treated with the anion of triethyl phosphonoacetate generated with a base such as, but not limited to, sodium hydride to provide an intermediate which is then hydrogenated in the presence of a catalyst such as, but not limited to, palladium or platinum, to provide esters of formula (30). Esters of formula (30) can be treated with a reducing agent such as, but not limited to, lithium aluminum hydride or sodium borohydride to provide alcohols of formula (31). Alcohols of formula (31) can be converted to compounds of formula (32) using the transformation as outlined in Scheme 3, employing the reaction conditions used in the conversion of compounds of formula (19) to compounds of formula (10). Compounds of formula (32) can be converted to compounds of formula (35) using the reaction conditions outlined in Scheme 1 for the transformation of compounds of formula (5) to compounds of formula (9). Separation of products of formula (30) using for instance, column chromatography, provides the pure trans-cyclobutane esters of formula (33) and the pure cis-cyclobutane esters of formula (34). The esters of formulas (33) and (34) can then separately, be converted to the amines of formula (36) and (37) using the conditions for the conversion of compounds of formula (30) to compounds of formula (35).

Scheme 8

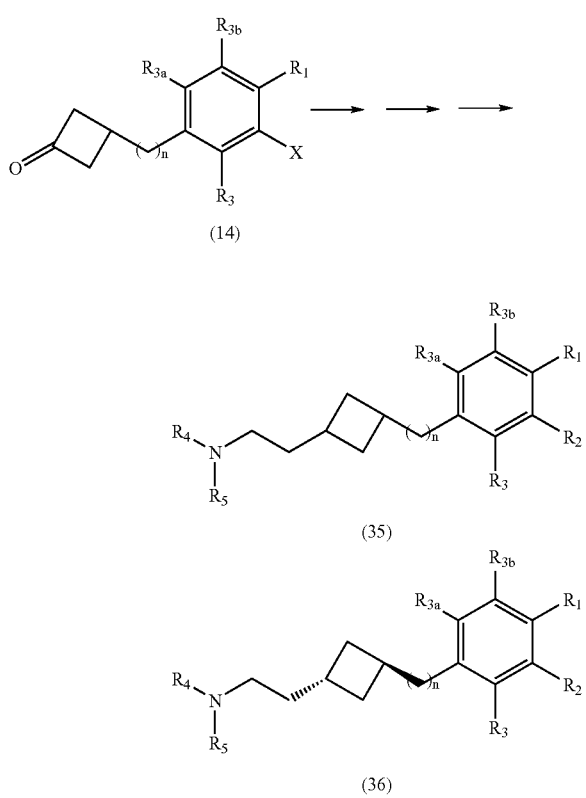

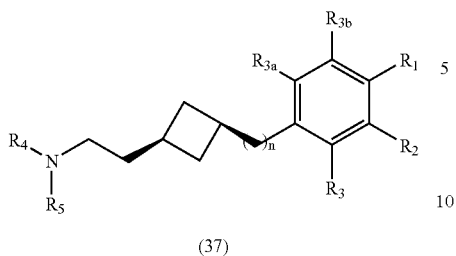

(37)

Likewise compounds of formulas (35), (36), and (37), wherein n, $R_3$, $R_{3a}$, $R_{3b}$, $R_4$, and $R_5$ are as defined in formula (I); $R_1$ is hydrogen, alkyl, alkoxy, halogen, cyano, or thioalkoxy; and $R_2$ is -$L_2$-$R_{6a}$-$L_3$-$R_{6b}$, wherein $L_2$ is a bond, —N(H), —N(alkyl), —O—, or —S—, and $R_{6a}$, $L_3$, and $R_{6b}$ are as defined in formula (I), can be prepared as described in Scheme 8. Cyclobutanones of formula (14) wherein X is Br, Cl or I, can be converted to amines of formulas (35), (36), and (37) using the reaction conditions as described in Scheme 7, except for substituting boronic acid or esters of formula (18) for (8) and pinacol borane reagents of formula (18a) for (8a) for the Suzuki reactions, and except for substituting organostannes of formula $(R_{102})_3SnR_2$ for $(R_{102})_3SnR_1$ for Stille coupling.

Alternatively, alkenes of formula (1), wherein n, $R_3$, $R_{3a}$, and $R_{3b}$, are as defined in formula (I); $R_2$ is hydrogen, alkyl, alkoxy, halogen, cyano, or thioalkoxy; and X is Cl, Br, or I can be treated with 1-acetyl pyrrolidine and triflate anhydride in the presence of a base such as, but not limited to, lutidine, followed by in situ hydrolysis, to provide cyclobutanones of formula (3). References that describe this methodology may be found in the following: L. Ghosez et al., Tetrahedron Lett., 27:5211-5214(1986); I. Marko et al., J. Amer. Chem. Soc., 107:2192(1981); C. Houge et al., J. Amer. Chem. Soc., 104: 2920(1982); J. B. Falmagre et al., Angew. Chem. Int. Ed., 20:879(1981).

Likewise, cyclobutanones of formula (14), wherein n, $R_3$, $R_{3a}$, and $R_{3b}$, are as defined in formula (I); $R_1$ is hydrogen, alkyl, alkoxy, halogen, cyano, or thioalkoxy; and X is Cl, Br, or I, can be prepared from alkenes of formula (12) using the reaction conditions as outlined above.

Scheme 9

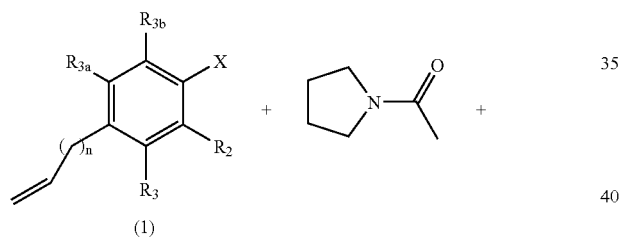

Scheme 10

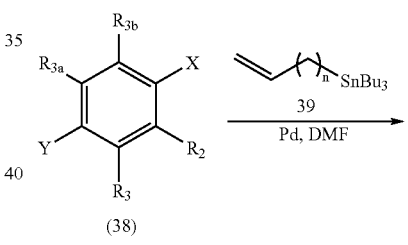

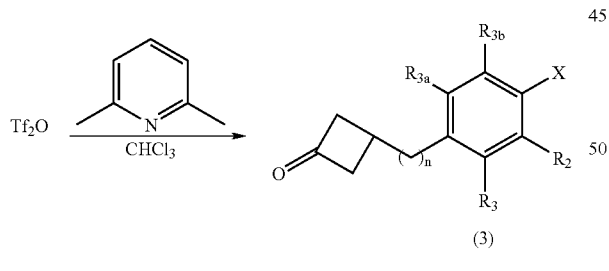

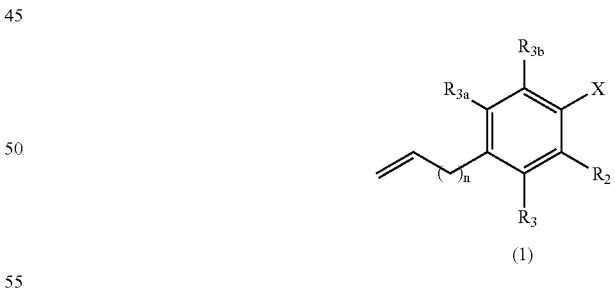

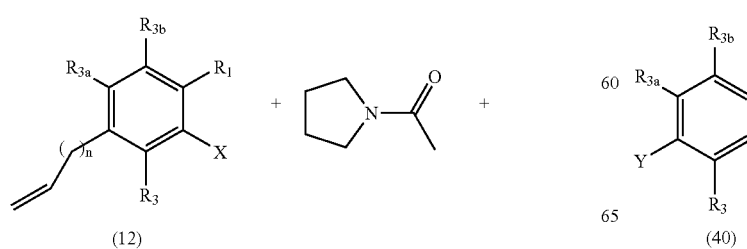

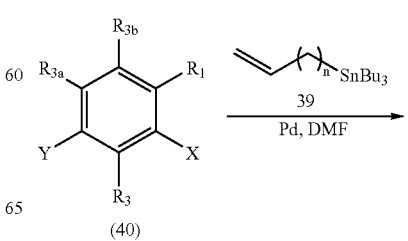

-continued

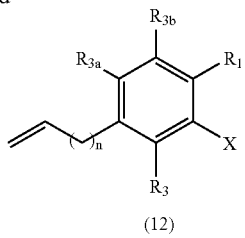

(12)

Alkenes of formula (1) wherein X is I, Br or Cl or hydroxy; n, $R_3$, $R_{3a}$, and $R_{3b}$ are as defined in formula (I); and $R_2$ is hydrogen, alkyl, alkoxy, halogen, cyano, or thioalkoxy; can be purchased or prepared as described in Scheme 10. Halides of formula (38), wherein Y is I, Br, or triflate (prepared by the treatment of phenols with triflate anhydride), can be treated with tin reagent of formula (39) in the presence of a palladium source such as dichlorobis(triphenylphosphine)palladium(II) (CAS# 13965-03-2) or tris(dibenzylidineacetone)dipalladium (CAS # 52409-22-0) or palladium diacetate, and a ligand such as tri(2-furyl)phosphine (CAS # 5518-52-5) or triphenyl phosphine, in a solvent such as DMF at 25-150° C. to provide the alkenes of formula (1).

Alternatively, alkenes of formula (1) wherein n is 0 can be prepared through substituted benzaldehydes via Wittig reaction, which is well-known to those skilled in the art of organic synthesis. References that discribe these methods may be found in the following: S. Li et al., Chemische Berichte, 123:1441-1442(1990); T. Kauffmann et al., Tetrahedron Lett., 22:5031-5034(1981).

Likewise, alkenes of formula (12) wherein X is I, Br or Cl or hydroxy; n, $R_3$, $R_{3a}$, and $R_{3b}$ are as defined in formula (I); and $R_1$ is hydrogen, alkyl, alkoxy, halogen, cyano, or thioalkoxy; can be purchased or prepared using the reaction conditions outlined above.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzensulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart, et al. *J. Med. Chem.* 2005, 48, 38-55; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161; Yates, et al. JPET (1999) 289, 1151-1159 "Identification and Pharmacological Characterization of a Series of New 1H-4-Substituted-lmidazoyl Histamine $H_3$ Receptor Ligands"; Ligneau, et al. Journal of Pharmacology and Experimental Therapeutics (1998), 287, 658-666; Tozer, M. Expert Opinion Therapeutic Patents (2000) 10, page 1045; M. T. Halpern, "GT-2331" Current Opinion in Central and Peripheral Nervous System Investigational Drugs (1999) 1, pages 524-527; Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002); Glase, S. A., et al. "Attention deficit hyperactivity disorder: pathophysiology and design of new treatments." Annual Reports in Medicinal Chemistry (2002), 37 11-20; Schweitzer, J. B., and Holcomb, H. H. "Drugs under investigation for attention-deficit hyperactivity disorder" Current Opinion in Investigative Drugs (2002) 3, p. 1207.

The ability of the compounds of the invention, including, but not limited to, those specified in the examples, to treat dementia, and diseases with deficits of memory and learning, may be demonstrated by "Two novel and selective nonimidazole $H_3$ receptor antagonists A-304121 and A-317920: II. In vivo behavioral and neurophysiological characterization." Fox, G. B., et al. Journal of pharmacology and experimental therapeutics (2003 June), 305(3), 897-908; "Identification of novel $H_3$ receptor ($H_3R$) antagonist with cognition enhancing properties in rats." Fox, G. B.; Inflammation Research (2003), 52(Suppl. 1), S31-S32; Bernaerts, P., et al. "Histamine $H_3$ antagonist thioperamide dose-dependently enhances memory consolidation and reverses amnesia induced by dizocilpine or scopolamine in a one-trial inhibitory avoidance task in mice" Behavioural Brain Research 154 (2004) 211-219; Onodera, et al. Nauyn-Schmiedebergs' Arch. Pharmacol. (1998), 357, 508-513; Prast, et al. Brain Research (1996) 734, 316-318; Chen, et al. Brain Research (1999) 839, 186-189 "Effects of histamine on MK-801-induced memory deficits in radial maze performance in rats"; Passani, et al. "Central histaminergic system and cognition" Neuroscience and Biobehavioral Reviews (2000) 24, p107-113.

The ability of the compounds of the invention, including, but not limited to, those specified in the examples, to treat schizophrenia, cognitive deficits of schizophrenia, and cognitive deficits, may be demonstrated by Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190 and by "Enhancement of prepulse inhibition of startle in mice by the $H_3$ receptor antagonists thioperamide and ciproxifan." Browman, Kaitlin E., et al. Behavioural Brain Research (2004), 153(1), 69-76; "$H_3$ receptor blockade by thioperamide enhances cognition in rats without inducing locomotor sensitization"; Komater, V. A., et al. Psychopharmacology (Berlin, Germany) (2003), 167(4), 363-372; A A Rodrigues, F P Jansen, R Leurs, H Timmerman and G D Prell, "Interaction of clozapine with the histamine $H_3$ receptor in rat brain" British Journal of Pharmacology (1995), 114(8), pp. 1523-1524; Passani, et al. "Central histaminergic system and cognition" Neuroscience and Biobehavioral Reviews (2000) 24, p107-113; Morriset, S., et al. "Atypical Neuroleptics Enhance Histamine Turnover in Brain Via 5-Hydroxytryptamine$_{2A}$ Receptor Blockade" Journal of Pharmacology and Experimental Therapeutics (1999) 288, pages 590-596.

The ability of the compounds of the invention, including, but not limited to, those specified in the examples, to treat dysfunction in psychiatric disorders, Alzheimer's disease, and mild cognitive impairment may be demonstrated by Meguro, et al. Pharmacology, Biochemistry and Behavior (1995) 50(3), 321-325; Esbenshade, T., et al. "Pharmacological and behavioral properties of A-349821, a selective and potent human histamine H3 receptor antagonist" Biochemical Pharmacology 68 (2004) 933-945; Huang, Y.-W., et al. "Effect of the histamine H3-antagonist clobenpropit on spatial memory deficits induced by MK-801 as evaluated by radial maze in Sprague-Dawley rats" Behavioural Brain Research 151 (2004) 287-293; Mazurkiewicz-Kwilecki and Nsonwah, Can. J. Physiol. Pharmacol. (1989) 67, p. 75-78; P. Panula, et al., Neuroscience (1997) 82, 993-997; Haas, et al., Behav. Brain Res. (1995) 66, p. 41-44; De Almeida and Izquierdo, Arch. Int. Pharmacodyn. (1986), 283, p. 193-198; Kamei et al., Psychopharmacology, (1990) 102, p. 312-318; Kamei and Sakata, Jpn. J. Pharmacol. (1991), 57, p. 437-482; Schwartz et al., Psychopharmacology, The Fourth Generation of Progress. Bloom and Kupfer (eds). Raven Press, New York, (1995) 397; and Wada, et al., Trends in Neurosci. (1991) 14, p. 415.

The ability of the compounds of the invention, including, but not limited to, those specified in the examples, to treat epilepsy, and seizures, may be demonstrated by Harada, C., et al. "Inhibitory effect of iodophenpropit, a selective histamine H3 antagonist, on amygdaloid kindled seizures" Brain Research Bulletin (2004) 63 p, 143-146; as well as by Yokoyama, et al., Eur. J. Pharmacol. (1993) 234, p. 129-133; Yokoyama, et al. European Journal of Pharmacology (1994) 260, p. 23; Yokoyama and Iinuma, CNS Drugs (1996) 5, p. 321; Vohora, Life Sciences (2000) 66, p. 297-301; Onodera et al., Prog. Neurobiol. (1994) 42, p. 685; Chen, Z., et al. "Pharmacological effects of carcinine on histaminergic neurons in the brain" British Journal of Pharmacology (2004) 143, 573-580; R. Leurs, R. C. Vollinga and H. Timmerman, "The medicinal chemistry and therapeutic potential of ligands of the histamine $H_3$ receptor", Progress in Drug Research (1995) 45, p. 170-165; Leurs and Timmerman, Prog. Drug Res. (1992) 39, p. 127; H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995); Yawata, et al. "Role of histaminergic neurons in development of epileptic seizures in EL mice" Molecular Brain Research 132 (2004) 13-17.

The ability of the compounds of the invention, including, but not limited to, those specified in the examples, to treat allergic rhinitis, and asthma, may be demonstrated by McLeod, R. L., Mingo, G. G., Herczku, C., DeGennaro-Culver, F., Kreutner, W., Egan, R. W., Hey, J. A., "Combined histamine H1 and H3 receptor blockade produces nasal decongestion in an experimental model of nasal congestion" Am. J. Rhinol. (1999a) 13, p. 391-399; McLeod, Robbie L.; Egan, Robert W.; Cuss, Francis M.; Bolser, Donald C.; Hey, John A. (Allergy, Schering-Plough Research Institute, Kenilworth, N.J., USA. ) Progress in Respiratory Research (2001), 31 (in *New Drugs for Asthma, Allergy and COPD*), pp. 133-136; A. Delaunois A., et al., "Modulation of acetylcholine, capsaicin and substance P effects by histamine $H_3$ receptors in isolated perfused rabbit lungs," European Journal of Pharmacology (1995) 277, p. 243-250; Dimitriadou, et al., "Functional relationship between mast cells and C-sensitive nerve fibres evidenced by histamine $H_3$-receptor modulation in rat lung and spleen," Clinical Science (1994), 87, p. 151-163.

The ability of the compounds of the invention, including, but not limited to, those specified in the examples, to treat motion sickness, dizziness, Meniere's disease, vestibular disorders, and vertigo, may be demonstrated by Pan, et al. Methods and Findings in Clinical Pharmacology (1998), 20(9), 771-777; O'Neill, et al. Methods and Findings in Clinical Pharmacology (1999) 21(4), 285-289; and by R. Leurs, R. C. Vollinga and H. Timmerman, "The medicinal chemistry and therapeutic potential of ligands of the histamine $H_3$ receptor," Progress in Drug Research (1995), 45, p. 170-165, Lozada, et al. "Plasticity of histamine $H_3$ receptor expression and binding in the vestibular nuclei after labyrinthectomy in rat" BioMedCentral Neuroscience 2004, 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A. A. "Antiobesity effects of A-331440, a novel non-imidazole histamine H3 receptor antagonist" European Journal of Pharmacology (2004) 487, 183-197; Hancock, A. A., et al. "Histamine $H_3$ antagonists in models of obesity" Inflamm. res. (2004) 53, *Supplement* 1 S47-S48; as well as by E. Itoh, M. Fujimiay, and A. Inui, "Thioperamide, A histamine $H_3$ receptor antagonist, powerfully suppresses peptide YY-induced food intake in rats," Biol. Psych. (1999) 45(4), p. 475-481; S. I. Yates, et al., "Effects of a novel histamine $H_3$ receptor antagonist, GT-2394, on food intake and weight gain in Sprague-Dawley rats," Abstracts, Society for Neuroscience, 102.10:219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000); Sakata T; et al. "Hypothalamic neuronal histamine modulates ad libitum feeding by rats." Brain research (1990 Dec. 24), 537(1-2), 303-6.

The ability of the compounds of the invention, including, but not limited to, those specified in the examples, to treat pain, including neuropathic pain and neuropathy, may be demonstrated by Malmberg-Aiello, Petra; Lamberti, Claudia; Ghelardini, Carla; Giotti, Alberto; Bartolini, Alessandro. British Journal of Pharmacology (1994), 111(4), 1269-1279; Hriscu, Anisoara; Gherase, Florenta; Pavelescu, M.; Hriscu, E. "Experimental evaluation of the analgesic efficacy of some antihistamines as proof of the histaminergic receptor involvement in pain." Farmacia, (2001), 49(2), 23-30, 76.

The ability of the compounds of the invention, including, but not limited to, those specified in the examples, to treat sleep disorders, including narcolepsy and pathological sleepiness, and jet lag, may be demonstrated by Barbier, A. J., et al. "Acute wake-promoting actions of JNJ-5207852, a novel, diamine-based $H_3$ antagonist" British Journal of Pharmacology (2004) 1-13; Monti et al., Neuropsychopharmacology (1996) 15, 31-35; Lin et al., Brain Res. (1990) 523, p. 325-330; Monti, et al., Neuropsychopharmacology (1996) 15, p. 31-35; Ligneau, et al. Journal of Pharmacology and Experimental Therapeutics (1998), 287, 658-666; Sakai, et al., Life Sci. (1991) 48, p. 2397-2404; Mazurkiewicz-Kwilecki and Nsonwah, Can. J. Physiol. Pharmacol., (1989) 67, p. 75-78; P. Panula, et al., Neuroscience (1998) 44, 465-481; Wada, et al., Trends in Neuroscience (1991) 14, p. 415; and Monti, et al., Eur. J. Pharmacol. (1991), 205, p. 283; Dvorak, C., et al. "4-Phenoxypiperidines: Potent, Conformationally Restricted, Non-Imidazole Histamine $H_3$ Antagonists" Journal of Medicinal Chemistry (2005) 48, 2229-2238.

The ability of the compounds of the invention, including, but not limited to, those specified in the examples, to treat drug abuse. Amphetamine is an abused stimulant in humans. It, and similar abused drugs stimulate locomotor activity in animals, and it has been found that the $H_3$ antagonist thioperamide suppresses the locomotor stimulation induced by amphetamine; therefore H₃ antagonists are likely to be useful for treating drug abuse as may be demonstrated by Clapham J.; Kilpatrick G. J. "Thioperamide, the selective histamine H₃ receptor antagonist, attenuates stimulant-induced locomotor activity in the mouse", European journal of pharmacology (1994), 259(2), 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti, et al. British Journal of Pharmacology (1998) 123, 1331-1336; Perez-Garcia C, et. al., Psychopharmacology (Berlin) (1999) 142(2):215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sánchez-Lemus, E., et al. "Histamine H₃ receptor activation inhibits dopamine $D_1$ receptor-induced cAMP accumulation in rat striatal slices" Neuroscience Letters (2004) 364, p. 179-184; Sakai, et al., Life Sci. (1991) 48, 2397-2404; Fox, G. B., et al. "Pharmacological Properties of ABT-239: II. Neurophysiological Characterization and Broad Preclinical Efficacy in Cognition and Schizophrenia of a Potent and Selective Histamine H₃ Receptor Antagonist" Journal of Pharmacology and Experimental Therapeutics, 313:176-190, 2005; Chen, Z., et al. "Pharmacological effects of carcinine on histaminergic neurons in the brain" British Journal of Pharmacology (2004) 143, 573-580.

The ability of the compounds of the invention, including, but not limited to, those specified in the examples, to treat medullary thyroid carcinoma, melanoma, polycystic ovary syndrome, may be demonstrated by Polish Med. Sci. Mon. (1998) 4(5): 747; Adam Szelag, "Role of histamine H₃-receptors in the proliferation of neoplastic cells in vitro," Med. Sci. Monitor (1998) 4(5):747-755; and C. H. Fitzsimons, et al., "Histamine receptors signalling in epidermal tumor cell lines with H-ras gene alterations," Inflammation Res. (1998) 47 (Suppl 1):S50-S51.

Compounds of the invention are particularly useful for treating and preventing a condition or disorder affecting memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.01 to about 0.1 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Example 1

4'-{3-[(2R)-2-Methyl-pyrrolidin-1-yl]-trans-cyclobutyl}-biphenyl-4-carbonitrile

Example 1A 3-(4-Bromo-phenyl)-cis-cyclobutanol

To a solution of 3-(4-bromo-phenyl)-cyclobutanone (3 g, 13.3 mmol) (J. Med. Chem., 43:721-735(2000)), in anhydrous ether (100 mL) cooled to −20° C. was dropwise added lithium aluminum hydride (1M in THF, 15 mL). The mixture was then allowed to warm to room temperature and stirred for 4 hours. The reaction was slowly quenched with NaOH (1M, 0.8 mL), H₂O (0.8 mL) and NaOH (1M, 0.8 mL) sequentially. After stirring for about 30 minutes, the mixture was filtered through a layer of diatomaceous earth and washed with extra ether (100 mL). The filtrate was evaporated under reduced pressure to provide a colorless oil as the title compound (3.01 g, 100%). ¹H NMR (300 MHz, CDCl₃) δ 2.0 (m, 2 H), 2.76 (m, 2 H), 2.92 (m, 1 H), 4.28 (m, 1 H), 7.09 (d, J=9 Hz, 2 H), 7.41 (d, J=9 Hz, 2 H); (DCl/NH₃) m/z 244(M+NH₄)⁺.

Example 1B

1-[3-(4-Bromo-phenyl)-trans-cyclobutyl]-(2R)-2-methyl-pyrrolidine

The product from Example 1A (3 g, 13.2 mmol) was dissolved in anhydrous dichloromethane (120 mL) and cooled to 0° C. The solution was treated with $K_2CO_3$ (5.46 g, 39.6 mmol), followed by trifluoroacetic acid anhydride (3.35 mL, 19.8 mmol), and stirred at room temperature for three hours. The reaction mixture was treated with a solution of (R)-2-methylpyrrolidine (prepared according to the procedure that described in: R. Altenbach et al., WO 2004043458, and Y. Pu et al., Organic Process Research & Development, 9(1), 45-50, 2005) (2 g, 23.7 mmol) in toluene, stirred overnight and partitioned between dichloromethane and $H_2O$. The organic extraction was dried ($MgSO_4$), filtered, concentrated and chromatographed on silica gel eluting with a gradient of 1% to 2% (9:1 MeOH:concentrated $NH_4OH$) in dichloromethane, providing the title compound as a brownish oil (1.3 g, 34%). $^1H$ NMR (400 MHz, $CD_3OD$) δ 1.11 (d, J=9 Hz, 3 H), 1.46 (m, 1 H), 1.78 (m, 2 H), 1.98 (m, 1 H), 2.20 (m, 1 H), 2.35 (m, 2 H), 2.58 (m, 3 H), 3.03 (m, 1 H), 3.34 (m, 1 H), 3.47 (m, 1 H), 7.23 (d, J=9 Hz, 2 H), 7.44 (d, J=9 Hz, 2 H); ($DCl/NH_3$) m/z 294 $(M+H)^+$.

Example 1C

4'-{3-[(2R)-2-Methyl-pyrrolidin-1-yl]-trans-cyclobutyl}-biphenyl-4-carbonitrile To a solution of the product from Example 1B (50 mg, 0.17 mmol) in isopropyl alcohol (4 mL) under an atmosphere of nitrogen was added 4-cyanophenylboronic acid (30 mg, 0.2 mmol), dichlorobis(triphenylphosphine)palladium(II) (6 mg, 8.5 μmol), and potassium carbonate (59 mg, 0.43 mmol). The mixture was heated at 90° C. for 5 hrs, cooled to ambient temperature and partitioned between ethyl acetate (25 mL) and $H_2O$ (10 mL). The organic extraction was washed with brine, dried ($MgSO_4$), filtered, concentrated, and chromatographed on silica gel eluting with 3% (9:1 MeOH:concentrated $NH_4OH$) in dichloromethane to provide 41 mg of the title compound. $^1H$ NMR (400 MHz, $CD_3OD$) δ 1.15 (d, J=6 Hz, 3 H), 1.49 (m, 1 H), 1.79 (m, 2 H), 2.01 (m, 1 H), 2.29 (m, 1 H), 2.43 (m, 2 H), 2.63 (m, 3 H), 3.07 (m, 1 H), 3.43 (m, 1 H), 3.54 (m, 1 H), 7.41 (d, J=9 Hz, 2 H), 7.62 (d, J=9 Hz, 2 H), 7.75 (AB q, 4 H); ($DCl/NH_3$) m/z 317 $(M+H)^+$.

Example 2

4'-{3[(2R)-2-Methyl-pyrrolidin-1-yl]-cis-cyclobutyl}-biphenyl-4-carbonitrile

Example 2A

1-[3-(4-Bromo-phenyl)-cis-cyclobutyl]-(2R)-2-methyl-pyrrolidine

To a solution of 3-(4-bromo-phenyl)-cyclobutanone (1 g, 4.44 mmol) in ethanol (20 mL) was added a solution of (R)-2-methylpyrrolidine (prepared according to the procedure that described in: R. Altenbach et al., WO 2004043458, and Y. Pu et al., Organic Process Research & Development, 9(1), 45-50, 2005) (0.75 g, 8.9 mmol) in toluene. Borane-pyridine complex (0.67 mL, 6.6 mmol) was added subsequently and stirred at ambient temperature for 16 hours. The mixture was concentrated under reduced pressure to dryness and partitioned between ethyl acetate and $H_2O$. The organic layers were washed with brine, dried ($MgSO_4$) and concentrated under reduced pressure. Chromatography of the residue eluting with a gradient of 1-2% (9:1 MeOH:concentrated $NH_4OH$) in dichloromethane provided the title compound (680 mg, 52%) as the faster eluting component and the product from Example 1B (76 mg, 6%) as the slower eluting component. $^1H$ NMR (300 MHz, $CD_3OD$) δ 1.15 (d, J=6 Hz, 3 H), 1.46 (m, 1 H), 1.77 (m, 2 H), 1.99 (m, 1 H), 2.07 (m, 2 H), 2.34 (m, 1 H), 2.58 (m, 3 H), 3.04 (m, 2 H), 3.17 (m, 1 H), 7.17 (d, J=9 Hz, 2 H), 7.41 (d, J=9 Hz, 2 H); ($DCl/NH_3$) m/z 294 $(M+H)^+$.

Example 2B

4'-{3[(2R)-2-Methyl-pyrrolidin-1-yl]-cis-cyclobutyl}-biphenyl-4-carbonitrile A solution of the product from Example 2A (100 mg, 0.34 mmol), 4-cyanophenyl boronic acid (65 mg, 0.44 mmol), dichlorobis(triphenylphosphine)palladium(II) (12 mg, 17 μmol) and potassium carbonate (120 mg, 0.85 mmol) under an atmosphere of nitrogen in isopropyl alcohol (8 mL) was heated at reflux for 5 hrs. Then, the reaction mixture was cooled to ambient temperature. The mixture was partitioned between ethyl acetate (25 mL) and $H_2O$ (10 mL). The organic layer was washed with brine, dried with magnesium sulfate, filtered, concentrated, and chromatographed on silica gel, eluting with 3% (9:1 MeOH:conc $NH_4OH$) in dichloromethane to provide 36 mg of the title compound. $^1H$ NMR (300 MHz, $CD_3OD$) δ 1.21 (d, J=6 Hz, 3 H), 1.54 (m, 1 H), 1.84 (m, 2 H), 2.07 (m, 1 H), 2.18 (m, 2 H), 2.57 (m, 2 H), 2.71 (m, 2 H), 3.11 (m, 1 H), 3.27 (m, 2 H), 7.39 (d, J=9 Hz, 2 H), 7.64 (d, J=9 Hz, 2 H), 7.79 (s, 4 H); ($DCl/NH_3$) m/z 317 $(M+H)^+$.

Example 3

4'-[3-(2-Methyl-pyrrolidin-1-yl)-cis-cyclobutyl]-biphenyl-4-carbonitrile

Example 3A

1-[3-(4-Bromo-phenyl)-cis-cyclobutyl]-2-methyl-pyrrolidine

The title compound was prepared using the procedure described in Example 2A except substituting racemic 2-methylpyrrolidine for (R)-2-methylpyrrolidine. $^1H$ NMR (300 MHz, $CD_3OD$) δ 1.16 (d, J=6 Hz, 3 H), 1.46 (m, 1 H), 1.78 (m, 2 H), 2.08 (m, 3 H), 2.39 (m, 1 H), 2.49 (m, 1 H), 2.61 (m, 2 H), 3.07 (m, 3 H), 7.17 (d, J=9 Hz, 2 H), 7.42 (d, J=9 Hz, 2 H); ($DCl/NH_3$) m/z 294 $(M+H)^+$.

Example 3B

4'-[3-(2-Methyl-pyrrolidin-1-yl)-cis-cyclobutyl]-biphenyl-4-carbonitrile

The title compound was prepared using the procedure described in Example 2B except substituting the product from Example 3A for the product from Example 2A. $^1H$ NMR (300 MHz, $CD_3OD$) δ 1.22 (d, J=6 Hz, 3 H), 1.54 (m, 1 H), 1.84 (m, 2 H), 2.05 (m, 1 H), 2.19 (m, 2 H), 2.57 (m, 2

H), 2.71 (m, 2 H), 3.27 (m, 3 H), 7.39 (d, J=9 Hz, 2 H), 7.63 (d, J=9 Hz, 2 H), 7.79 (s, 4 H); (DCl/NH$_3$) m/z 317 (M+H)$^+$.

Example 4

(±)4'-[3-(2-Methyl-pyrrolidin-1-yl)-trans-cyclobutyl]-biphenyl-4-carbonitrile

Example 4A (±)1-[3-(4-Bromo-phenyl)-trans-cyclobutyl]-2-methyl-pyrrolidine

The title compound was prepared using the procedure described in Example 1B except substituting racemic 2-methylpyrrolidine for (R)-2-methylpyrrolidine. $^1$H NMR (300 MHz, CD$_3$OD) δ 1.24 (d, J=6 Hz, 3 H), 1.60 (m, 1 H), 1.90 (m, 2 H), 2.12 (m, 1 H), 2.36 (m, 1 H), 2.45 (m, 1 H), 2.67 (m, 3 H), 2.96 (m, 1 H), 3.24 (m, 1 H), 3.60 (m, 2 H), 7.25 (d, J=9 Hz, 2 H), 7.46 (d, J=9 Hz, 2 H); (DCl/NH$_3$) m/z 294 (M+H)$^+$.

Example 4B (±)4'-[3-(2-Methyl-pyrrolidin-1-yl)-trans-cyclobutyl]-biphenyl-4-carbonitrile The title compound was prepared using the procedure described in Example 2B except substituting the product from the Example 4A for the product from Example 2A. $^1$H NMR (300 MHz, CD$_3$OD) δ 1.24 (d, J=6 Hz, 3 H), 1.60 (m, 1 H), 1.90 (m, 2 H), 2.12 (m, 1 H), 2.41 (m, 1 H), 2.53 (m, 1 H), 2.70 (m, 3 H), 2.92 (m, 1 H), 3.24 (m, 1 H), 3.62 (m, 2 H), 7.46 (d, J=9 Hz, 2 H), 7.67 (d, J=9 Hz, 2 H), 7.80 (s, 4H); (DCl/NH$_3$) m/z 317 (M+H)$^+$.

Example 5

5-{4-[3-({2R}-2-Methyl-pyrrolidin-1-yl)-cis-cyclobutyl]-phenyl}-pyrimidine

The title compound was prepared using the procedure described in Example 2B except substituting 5-pyrimidineboronic acid (CAS # 109299-78-7) for 4-cyanophenylboronic acid. $^1$H NMR (300 MHz, CD$_3$OD) δ 1.22 (d, J=6 Hz, 3 H), 1.54 (m, 1 H), 1.85 (m, 2 H), 2.07 (m, 1 H), 2.19 (m, 2 H), 2.57 (m, 2 H), 2.72 (m, 2 H), 3.15 (m, 1 H), 3.26 (m, 2 H), 7.45 (d, J=9 Hz, 2 H), 7.68 (d, J=9 Hz, 2 H), 9.05 (s, 2 H), 9.11 (s, 1 H); (DCl/NH$_3$) m/z 294 (M+H)$^+$.

Example 6

2,6-Difluoro-3-{4-[3-({2R}-2-methyl-pyrrolidin-1-yl)-cis-cyclobutyl]-phenyl}-pyridine The title compound was prepared using the procedure described in Example 2B except substituting 2,6-difluoropyridine-3-boronic acid (CAS # 136466-94-9) for 4-cyanophenylboronic acid. $^1$H NMR (300 MHz, CD$_3$OD) δ 1.24 (d, J=6 Hz, 3 H), 1.55 (m, 1 H), 1.87 (m, 2 H), 2.08 (m, 1 H), 2.21 (m, 2 H), 2.60 (m, 2 H), 2.74 (m, 1 H), 2.84 (m, 1 H), 3.18 (m, 1 H), 3.29 (m, 2 H), 7.06 (dd, J=9 Hz, J=3 Hz, 1 H), 7.38 (d, J=9 Hz, 2 H), 7.51 (dd, J=9 Hz, J=3 Hz, 2 H), 8.14 (dd, J=18 Hz, J=9 Hz, 1 H); (DCl/NH$_3$) m/z 329 (M+H)$^+$.

Example 7

2,6-Difluoro-3-{4-[3-({2R}-2-methyl-pyrrolidin-1-yl)-trans-cyclobutyl]-phenyl}-pyridine The title compound was prepared using the procedure described in Example 1C except substituting 2,6-difluoropyridine-3-boronic acid (CAS # 136466-94-9) for 4-cyanophenylboronic acid. $^1$H NMR (300 MHz, CD$_3$OD) δ 1.28 (d, J=6 Hz, 3 H), 1.61 (m, 1 H), 1.93 (m, 2 H), 2.14 (m, 1 H), 2.45 (m, 1 H), 2.55 (m, 1 H), 2.73 (m, 3 H), 3.04 (m, 1 H), 3.32 (m, 1 H), 3.64 (m, 2 H), 7.07 (dd, J=9 Hz, J=3 Hz, 1 H), 7.46 (d, J=9 Hz, 2 H), 7.55 (dd, J=9 Hz, J=3 Hz, 2 H), 8.16 (dd, J=18 Hz, J=9 Hz, 1 H); (DCl/NH$_3$) m/z 329 (M+H)$^+$.

Example 8

2,6-Dimethyl-3-{4-[3-({2R}-2-methyl-pyrrolidin-1-yl)-trans-cyclobutyl]-phenyl}-pyridine The title compound was prepared using the procedure described in Example 1C except substituting 2,6-dimethylpyridine-3-boronic acid for 4-cyanophenylboronic acid. $^1$H NMR (300 MHz, CD$_3$OD) δ 1.23 (d, J=6 Hz, 3 H), 1.56 (m, 1 H), 1.88 (m, 2 H), 2.09 (m, 1 H), 2.39 (m, 1 H), 2.50 (m, 1 H), 2.43 (s, 3 H), 2.45 (s, 3 H), 2.69 (m, 3 H), 2.86 (m, 1 H), 3.22 (m, 1 H), 3.64 (m, 2 H), 7.17 (d, J=6 Hz, 1 H), 7.30 (d, J=9 Hz, 2 H), 7.42 (d, J=9 Hz, 2 H), 7.52 (d, J=6 Hz, 1 H); (DCl/NH$_3$) m/z 321 (M+H)$^+$.

Example 9

2,6-Dichloro-3-{4-[3-({2R}-2-methyl-pyrrolidin-1-yl)-trans-cyclobutyl]-phenyl}-pyridine The title compound was prepared using the procedure described in Example 1C except substituting 2,6-dichloropyridine-3-boronic acid (CAS # 148493-34-9) for 4-cyanophenylboronic acid. $^1$H NMR (300 MHz, CD$_3$OD) δ 1.22 (d, J=6 Hz, 3 H), 1.60 (m, 1 H), 1.88 (m, 2 H), 2.08 (m, 1 H), 2.38 (m, 1 H), 2.51 (m, 1 H), 2.69 (m, 3H), 2.85 (m, 1 H), 3.18 (m, 1 H), 3.61 (m, 2 H), 7.44 (s, 4 H), 7.49 (d, J=9 Hz, 1 H), 7.81 (d, J=9 Hz, 1 H); (DCl/NH$_3$) m/z 362 (M+H)$^+$.

Example 10

4'-{3-[(2S)-2-Methyl-pyrrolidin-1-yl]-cis-cyclobutyl}-biphenyl-4-carbonitrile

The title compound was prepared using the procedure described in Example 2, except substituting (S)-2-methylpyrrolidine (prepared according to the procedure that described in: R. Altenbach et al., WO 2004043458, and Y. Pu et al., Organic Process Research & Development, 9(1), 45-50, 2005) for (R)-2-methylpyrrolidine in Example 2A. $^1$H NMR (300 MHz, CD$_3$OD) δ 1.31 (d, J=6 Hz, 3 H), 1.65 (m, 1 H), 1.95 (m, 2 H), 2.26 (m, 3 H), 2.68 (m, 1 H), 2.78 (m, 2 H), 3.26 (m, 4 H), 7.40 (d, J=9 Hz, 2 H), 7.65 (d, J=9 Hz, 2 H), 7.79(s, 4 H); (DCl/NH$_3$) m/z 317 (M+H)$^+$.

Example 11

5-{4-[3-({2R}-2-Methyl-pyrrolidin-1-yl)-trans-cyclobutyl]-phenyl}-pyrimidine

The title compound was prepared using the procedure described in Example 1C except substituting 5-pyrimidineboronic acid (CAS # 109299-78-7) for 4-cyanophenylboronic acid. $^1$H NMR (300 MHz, CD$_3$OD) δ 1.17 (d, J=6 Hz, 3 H), 1.54 (m, 1 H), 1.83 (m, 2 H), 2.05 (m, 1 H), 2.32 (m, 1 H), 2.50 (m, 2 H), 2.66 (m, 3 H), 3.10 (m, 1 H), 3.48 (m, 1 H), 3.58 (m, 1 H), 7.51 (d, J=9 Hz, 2 H), 7.69 (d, J=9 Hz, 2 H), 9.05 (s, 2 H), 9.11 (s, 1 H); (DCl/NH$_3$) m/z 294 (M+H)$^+$.

Example 12

2-{4-[3-({2R}-2-Methyl-pyrrolidin-1-yl)-trans-cyclobutyl]-phenyl}-2H-pyridazin-3-one A solution of the product from Example 1B (40 mg, 0.14 mmol), 3(2H)-pyridazinone (CAS # 504-30-3, 20 mg, 0.2 mmol), copper (13 mg, 0.2 mmol), and potassium carbonate (38 mg, 0.27 mmol) in anhydrous DMF was heated to 140° C. under an atmosphere of nitrogen for 16 hours. Then, the reaction mixture was cooled to ambient temperature, treated with H$_2$O and extracted with ethyl acetate (2×25 mL). The organic layers were combined, washed with brine and dried with magnesium sulfate. After filtration, the organic layer was concentrated and the resulting oil was purified on preparative HPLC on a Waters™ Symmetry C8 column (25 mm×100 mm, 7 μm particle size) using a gradient of 10% to 100% acetonitrile:0.1% aqueous TFA over 8 min (10 min run time) at a flow rate of 40 mL/min to provide 5 mg of the title compound as a trifluoroacetic acid salt. $^1$H NMR (300 MHz, CD$_3$OD) δ 1.46 (d, J=6 Hz, 3 H), 1.78 (m, 1 H), 2.10 (m, 2 H), 2.33 (m, 1 H), 2.68 (m, 2 H), 2.81 (m, 2 H), 3.18 (m, 1 H), 3.59 (m, 2 H), 3.74 (m, 1 H), 4.10 (m, 1 H), 7.09 (dd, J=9 Hz, J=3 Hz, 1 H), 7.48 (d, J=9 Hz, 2 H), 7.50 (m, 1 H), 7.56 (d, J=9 Hz, 2 H), 8.04 (m, 1 H); (DCl/NH$_3$) m/z 310 (M+H)$^+$.

Example 13

4'-{3-[(2S)-2-Methyl-pyrrolidin-1-yl]-trans-cyclobutyl}-biphenyl-4-carbonitrile

Example 13A

1-[3-(4-Bromo-phenyl)-trans-cyclobutyl]-(2S)-2-methyl-pyrrolidine

The title compound was prepared using the procedure described in Example 1B except substituting (S)-2-methylpyrrolidine (prepared according to the procedure that described in: R. Altenbach et al., WO 2004043458, and Y. Pu et al., Organic Process Research & Development, 9(1), 45-50, 2005) for (R)-2-methylpyrrolidine in Example 1B. $^1$H NMR (300 MHz, CD$_3$OD) δ 1.13 (d, J=6 Hz, 3 H), 1.49 (m, 1 H), 1.79 (m, 2 H), 1.99 (m, 1 H), 2.23 (m, 1 H), 2.36 (m, 2 H), 2.59 (m, 3 H), 3.04 (m, 1 H), 3.36 (m, 1 H), 3.46 (m, 1 H), 7.24 (d, J=9 Hz, 2 H), 7.44 (d, J=9 Hz, 2 H); (DCl/NH$_3$) m/z 294 (M+H)$^+$.

Example 13B

4'-{3-[(2S)-2-Methyl-pyrrolidin-1-yl]-trans-cyclobutyl}-biphenyl-4-carbonitrile

The title compound was prepared using the procedure described in Example 1C except substituting the product from Example 13A for the product from Example 1B. $^1$H NMR (300 MHz, CD$_3$OD) δ 1.36 (d, J=6 Hz, 3 H), 1.72 (m, 1 H), 2.01 (m, 2 H), 2.24 (m, 1 H), 2.55 (m, 1 H), 2.63 (m, 1 H), 2.78 (m, 2 H), 3.02 (m, 1 H), 3.25 (m, 1 H), 3.42 (m, 1 H), 3.69 (m, 1 H), 3.90 (m, 1 H), 7.47 (d, J=9 Hz, 2 H), 7.68 (d, J=9 Hz, 2 H), 7.80 (AB q, 4 H); (DCl/NH$_3$) m/z 317 (M+H)$^+$.

Example 14

5-{4-[3-({2S}-2-Methyl-pyrrolidin-1-yl)-trans-cyclobutyl]-phenyl}-pyrimidine

The title compound was prepared using the procedure described in Example 1C, except substituting 5-pyrimidineboronic acid (CAS # 109299-78-7) for 4-cyanophenylboronic acid and substituting the product from Example 13A for the product from Example 1B. $^1$H NMR (300 MHz, CD$_3$OD) δ 1.17 (d, J=6 Hz, 3 H), 1.51 (m, 1 H), 1.83 (m, 2 H), 2.03 (m, 1 H), 2.33 (m, 1 H), 2.46 (m, 2 H), 2.65 (m, 3 H), 3.09 (m, 1 H), 3.46 (m, 1 H), 3.59 (m, 1 H), 7.50 (d, J=9 Hz, 2 H), 7.69 (d, J=9 Hz, 2 H), 9.06 (s, 2 H), 9.11 (s, 1 H); (DCl/NH$_3$) m/z 294 (M+H)$^+$.

Example 15

2,4-Dimethoxy-5-{4-[3-({2S}-2-methyl-pyrrolidin-1-yl)-trans-cyclobutyl]-phenyl}-pyrimidine The title compound was prepared using the procedure described in Example 1C, except substituting the product from Example 13A for the product from Example 1B and substituting 2,4-dimethoxypyrimidine-5-boronic acid (CAS # 89641-18-9) for 4-cyanophenylboronic acid. $^1$H NMR (300 MHz, CD$_3$OD) δ 1.30 (d, J=6 Hz, 3 H), 1.66 (m, 1 H), 1.87 (m, 2 H), 2.19 (m, 1 H), 2.47 (m, 1 H), 2.55 (m, 1 H), 2.73 (m, 3 H), 3.37 (m, 2 H), 3.63 (m, 1 H), 3.79 (m, 1 H), 4.04 (s, 6 H), 7.39 (d, J=9 Hz, 2 H), 7.50 (d, J=9 Hz, 2 H), 8.24 (s, 1 H); (DCl/NH$_3$) m/z 354 (M+H)$^+$.

Example 16

2-Methoxy-5-{4-[3-({2R}-2-methyl-pyrrolidin-1-yl)-trans-cyclobutyl]-phenyl}-pyrimidine Example 16A 3-(4-Bromo-phenyl)-cis-cyclobutanol To a solution of 3-(4-bromo-phenyl)-cyclobutanone (3 g, 13.3 mmol) (J. Med. Chem., 43:721-735(2000)), in anhydrous ether (100 mL) cooled to −20° C. was dropwise added lithium aluminum hydride (1M in THF, 15 mL). The mixture was then allowed to warm to room temperature and stirred for 4 hours. The reaction was slowly quenched with NaOH (1M, 0.8 mL), H$_2$O (0.8 mL) and NaOH (1M, 0.8 mL) sequentially. After stirring for about 30 minutes, the mixture was filtered through a layer of diatomaceous earth and washed with extra ether (100 mL). The filtrate was evaporated under reduced pressure to provide a colorless oil as the title compound (3.01 g, 100%). $^1$H NMR (300 MHz, CDCl$_3$) δ 2.0 (m, 2 H), 2.76 (m, 2 H), 2.92 (m, 1 H), 4.28 (m, 1 H), 7.09 (d, J=9 Hz, 2 H), 7.41 (d, J=9 Hz, 2 H); (DCl/NH$_3$) m/z 244 (M+NH$_4$)$^+$.

Example 16B

1-[3-(4-Bromo-phenyl)-trans-cyclobutyl]-(2R)-2-methyl-pyrrolidine

The product from Example 16A (3 g, 13.2 mmol) was dissolved in anhydrous dichloromethane (120 mL) and cooled to 0° C. The solution was treated with K$_2$CO$_3$ (5.46 g, 39.6 mmol), followed by trifluoroacetic acid anhydride (3.35 mL, 19.8 mmol), and stirred at room temperature for three hours. The reaction mixture was treated with a solution of (R)-2-methylpyrrolidine (prepared according to the procedure that described in WO 2004043458, and Y. Pu et al., Organic Process Research & Development, 9(1), 45-50, 2005) (2 g, 23.7 mmol) in toluene, stirred for 16 hours and partitioned between dichloromethane and H$_2$O. The organic extraction was dried (MgSO$_4$), filtered, concentrated and chromatographed on silica gel eluting with a gradient of 1% to 2% (9:1 MeOH:concentrated NH$_4$OH) in dichloromethane, providing the title compound as a brownish oil (1.3 g, 34%). $^1$H NMR (400 MHz, CD$_3$OD) δ 1.11 (d, J=9 Hz, 3 H), 1.46 (m, 1 H), 1.78 (m, 2 H), 1.98 (m, 1 H), 2.20 (m, 1 H), 2.35 (m, 2 H), 2.58 (m, 3 H), 3.03 (m, 1 H), 3.34 (m, 1 H), 3.47 (m, 1 H), 7.23 (d, J=9 Hz, 2 H), 7.44 (d, J=9 Hz, 2 H); (DCI/NH$_3$) m/z 294 (M+H)$^+$.

Example 16C

2-Methoxy-5-{4-[3-({2R}-2-methyl-pyrrolidin-1-yl)-trans-cyclobutyl]-phenyl}-pyrimidine To a solution of the product from Example 16B (50 mg, 0.17 mmol) in isopropyl alcohol (4 mL) under an atmosphere of nitrogen was added 2-methoxypyrimidine-5-boronic acid (Frontier Scientific, Inc., Logan, Utah, USA) (30 mg, 0.2 mmol), dichlorobis(triphenylphosphine)palladium(II) (6 mg, 8.5 µmol), and potassium carbonate (59 mg, 0.43 mmol). The mixture was heated at 90° C. for 5 hrs, cooled to ambient temperature and partitioned between ethyl acetate (25 mL) and H$_2$O (10 mL). The organic extraction was washed with brine, dried (MgSO$_4$), filtered, concentrated, and chromatographed on silica gel eluting with 3% (9:1 MeOH:concentrated NH$_4$OH) in dichloromethane to provide 41 mg of the title compound. $^1$H NMR (300 MHz, CD$_3$OD) δ 1.13 (d, J=6 Hz, 3 H), 1.47 (m, 1 H), 1.77 (m, 2 H), 1.99 (m, 1 H), 2.27 (m, 1 H), 2.41 (m, 2 H), 2.62 (m, 3 H), 3.05 (m, 1 H), 3.38 (m, 1 H), 3.55 (m, 1 H), 4.05 (s, 3 H), 7.46 (d, J=9 Hz, 2 H), 7.59 (d, J=9 Hz, 2 H), 8.81 (s, 2 H); (DCI/NH$_3$) m/z 324 (M+H)$^+$.

Example 17

2,4-Dimethoxy-5-{4-[3-({2R}-2-methyl-pyrrolidin-1-yl)-trans-cyclobutyl]-phenyl}-pyrimidine The title compound was prepared using the procedure described in Example 1C except substituting 2,4-dimethoxy-pyrimidine-5-boronic acid (CAS # 89641-18-9) for 4-cyanophenylboronic acid. $^1$H NMR (300 MHz, CD$_3$OD) δ 1.20 (d, J=6 Hz, 3 H), 1.55 (m, 1 H), 1.85 (m, 2 H), 2.06 (m, 1 H), 2.34 (m, 1 H), 2.48 (m, 1 H), 2.66 (m, 4 H), 3.15 (m, 1 H), 3.36 (m, 1 H), 3.56 (m, 1 H), 4.04 (s, 6 H), 7.38 (d, J=9 Hz, 2 H), 7.47 (d, J=9 Hz, 2 H), 8.25 (s, 1 H); (DCI/NH$_3$) m/z 354 (M+H)$^+$.

Example 18

5-{4-[3-({2R}-2-Methyl-pyrrolidin-1-yl)-trans-cyclobutyl]-phenyl}-nicotinonitrile Example 18A 5-(4,4,5,5-Tetramethyl-[1,3,2]dioxaborolan-2-yl)-nicotinonitrile A mixture of 5-bromo-3-cyano pyridine (5 g), pinacolatodiborane (9.02 g, 1.3 eq), PdCl$_2$(dppf):CH$_2$Cl$_2$ (0.67 g, 0.03 eq), dppf (0.41 g, 0.03 eq) and potassium acetate (8.04 g, 3 eq) in dioxane (100 ml) was heated to 85° C. under nitrogen for 3 hours. The mixture was cooled to room temperature, diluted with 100 ml ethyl acetate and the solid was filtered off. The filtrate was concentrated to black oil (14.5 g). Chromatography (silica gel, 5:95 methanol:chloroform) gave yellow crystals (6.67 g). This was slurried with 60 ml hexane and the precipitate was filtered and vacuum dried at 45° C. to give the title compound (4.5 g).

Example 18B

5-{4-[3-({2R}-2-Methyl-pyrrolidin-1-yl)-trans-cyclobutyl]-phenyl}-nicotinonitrile The title compound was prepared using the procedure described in Example 1C except substituting the product of Example 18A for 4-cyanophenylboronic acid. $^1$H NMR (300 MHz, CD$_3$OD) δ 1.14 (d, J=6 Hz, 3 H), 1.50 (m, 1 H), 1.80 (m, 2 H), 2.01 (m, 1 H), 2.30 (m, 1 H), 2.43 (m, 2 H), 2.64 (m, 3 H), 3.07 (m, 1 H), 3.41 (m, 1 H), 3.57 (m, 1 H), 7.49 (d, J=9 Hz, 2 H), 7.70 d, J=9 Hz, 2 H), 8.45 (m, 1 H), 8.85 (d, J=3 Hz, 1 H), 9.08 (d, J=3 Hz, 1 H); (DCI/NH$_3$) m/z 318 (M+H)$^+$.

Example 19

2-Methyl-5-{4-[3-({2R}-2-methyl-pyrrolidin-1-yl)-trans-cyclobutyl]-phenyl}-benzothiazole Example 19A 2-Methyl-5-(4,4,5,5-tetramethyl-[1,3,2]dioxaborolan-2-yl)-benzothiazole A solution of 5-bromo-2-methyl-benzothiazole (2 g, 8.8 mmol), bis(pinacolato)diboron (2.7 g, 10.6 mmol), potassium acetate (3.1 g, 31.7 mmol) and Pd(dppf)$_2$Cl$_2$ dichloromethane complex (1:1) (360 mg, 0.51 mmol) in anhydrous tetrahydrofuran (70 mL) under a nitrogen atmosphere was heated to reflux overnight. After cooling to ambient temperature, the reaction mixture was filtered through diatomaceous earth and washed with ethyl acetate. The filtrate was washed with water and brine, dried (MgSO$_4$) and concentrated. The residue was chromatographed on silica gel eluting with 10% ethyl acetate in hexanes to provide the title compound as white crystals (1.96 g, 81%). $^1$H NMR (300 MHz, CD$_3$Cl$_3$) δ 1.37 (s, 12 H), 2.84 (s, 3 H), 7.75 (d, J=9 Hz, 1 H), 7.82 (d, J=9 Hz, 1 H), 8.38 (s, 1 H); (DCI/NH$_3$) m/z 276 (M+H)$^+$.

Example 19B

2-Methyl-5-{4-[3-({2R}-2-methyl-pyrrolidin-1-yl)-trans-cyclobutyl]-phenyl}-benzothiazole The title compound was prepared using the procedure described in Example 1C except substituting the product from Example 19A for 4-cyanophenylboronic acid. $^1$H NMR (300 MHz, CD$_3$OD) δ 1.14 (d, J=6 Hz, 3 H), 1.50 (m, 1 H), 1.80 (m, 2 H), 2.01 (m, 1 H), 2.28 (m, 1 H), 2.41 (m, 2 H), 2.62 (m, 3 H), 2.85 (s, 3 H), 3.04 (m, 1 H), 3.40 (m, 1 H), 3.55 (m, 1 H), 7.43 (d, J=9 Hz, 2 H), 7.67 (m, 3 H), 7.96 (d, J=9 Hz, 1 H), 8.09 (d, J=3 Hz, 1 H); (DCI/NH$_3$) m/z 363 (M+H)$^+$.

Example 20

2-Methyl-5-{4-[3-({2R}-2-methyl-pyrrolidin-1-yl)-trans-cyclobutyl]-phenyl}-pyridine The title compound was prepared using the procedure described in Example 1C except substituting 2-methyl-5-(4,4,5,5-tetramethyl-[1,3,2]dioxaborolan-2-yl)-pyridine (prepared according to the procedure described in J. Org. Chem. 67:7541-7543(2002)) for 4-cyanophenylboronic acid. $^1$H NMR (300 MHz, CD$_3$OD) δ 1.14 (d, J=6 Hz, 3 H), 1.49 (m, 1 H), 1.79 (m, 2 H), 2.01 (m, 1 H), 2.28 (m, 1 H), 2.42 (m, 2 H), 2.62 (m, 3 H), 3.05 (m, 1 H), 3.39 (m, 1 H), 3.53 (m, 1 H), 3.94 (s, 3 H), 6.88 (d, J=9 Hz, 1 H), 7.41 (d, J=9 Hz, 2 H), 7.54 (d, J=9 Hz, 2 H), 7.93 (dd, J=9 Hz, J=3 Hz, 1 H), 8.35 (d, J=3 Hz, 1 H); (DCl/NH$_3$) m/z 307 (M+H)$^+$.

Example 21

1,3,5-Trimethyl-4-{4-[3-(2-methyl-pyrrolidin-1-yl)-trans-cyclobutyl]-phenyl}-1H-pyrazole

Example 21A 1,3,5-Trimethyl-4-(4,4,5,5-tetramethyl-[1,3,2]dioxaborolan-2-yl)-1H-pyrazole A solution of 4-bromo-1,3,5-trimethyl-1H-pyrazole (1 g, 5.3 mmol) in anhydrous THF (20 mL) cooled to −78° C. under a nitrogen atmosphere was treated dropwise with n-butyl lithium (4.2 mL, 1.6 M in hexane) and stirred at room temperature for 20 minutes. Then, 2-isopropoxy-4,4,5,5-tetramethyl-[1,3,2]dioxaborolane (1.7 mL, 8.3 mmol) was added dropwise at −78° C. and allowed to warm to ambient temperature overnight. Ethyl acetate was added and the mixture was filtered through diatomaceous earth. The filtrate was concentrated and chromatographed on silica gel eluting with 40% ethyl acetate in hexanes to provide the title compound as white crystals (996 mg, 77%). $^1$H NMR (300 MHz, CDCl$_3$) δ 1.29 (s, 12 H), 2.33 (s, 3 H), 2.37 (s, 3 H), 3.69 (s, 3 H); (DCl/NH$_3$) m/z 237 (M+H)$^+$.

Example 21B 1,3,5-Trimethyl-4-{4-[3-(2-methyl-pyrrolidin-1-yl)-trans-cyclobutyl]-phenyl}-1H-pyrazole The title compound was prepared using the procedure described in Example 1C except substituting the product from Example 21A for 4-cyanophenylboronic acid. $^1$H NMR (300 MHz, CD$_3$OD) δ 1.17 (d, J=6 Hz, 3 H), 1.48 (m, 1 H), 1.80 (m, 2 H), 2.00 (m, 1 H), 2.17 (s, 3 H), 2.23 (s, 3 H), 2.28 (m, 1 H), 2.41 (m, 2 H), 2.62 (m, 3 H), 3.06 (m, 1 H), 3.41 (m, 1 H), 3.52 (m, 1 H), 3.75 (s, 3 H), 7.20 (d, J=9 Hz, 2 H), 7.36 (d, J=9 Hz, 2 H); (DCl/NH$_3$) m/z 324 (M+H)$^+$.

Example 22

5-{2-Fluoro-4-[3-({2R}-2-methyl-pyrrolidin-1-yl)-trans-cyclobutyl]-phenyl}-pyrimidinen

Example 22A

1-Bromo-2-fluoro-4-vinyl-benzene

A solution of 1-bromo-2-fluoro-4-iodo-benzene (1 g, 3.32 mmol), tributyl(vinyl)tin (0.97 mL, 3.32 mmol) and dichlorobis(triphenylphosphine)palladium(II) (116 mg, 0.17 mmol) in anhydrous DMF (3 mL) was heated in a microwave reactor to 160° C. for 5 minutes. Ether (20 mL) and H$_2$O (5 mL) were added and partitioned. The organic layer was washed with water, brine, dried (MgSO$_4$), filtered, and concentrated. The residue was chromatographed on silica gel eluting with hexanes to provide the title compound as a colorless oil (360 mg, 54%). $^1$H NMR (300 MHz, CDCl$_3$) δ 5.33 (d, J=9 Hz, 1 H), 5.76 (d, J=18 Hz, 1 H), 6.63 (dd, J=18 Hz, J=9 Hz, 1 H), 7.05 (dd, J=9 Hz, J=1 Hz, 1 H), 7.16 (dd, J=9 Hz, J=1 Hz, 1 H), 7.49 (t, J=9 Hz, 1 H); (DCl/NH$_3$) m/z 201 (M+H)$^+$.

Example 22B 3-(4-Bromo-3-fluoro-phenyl)-cyclobutanone

To a solution of the product from Example 22A (320 mg, 1.59 mmol) and a well stirred suspension of activated Zn—Cu, prepared according to the procedure described in J. Org. Chem., 43:2879-2882(1978), in anhydrous ether (20 mL) under nitrogen was added a solution of phosphorus oxychloride (0.22 mL, 2.38 mmol) and trichloroacetyl chloride (0.25 mL, 2.22 mmol) in anhydrous ether (20 mL) dropwise, and then stirred for two days. The reaction mixture was filtered through diatomaceous earth and washed with ether. The ethereal solution was concentrated in vacuo to ca. ¼ of its original volume. Pentane (100 mL) was added and the solution stirred for a few minutes to precipitate the zinc salts. The solution was decanted from the residue, washed successively with H$_2$O, a cold saturated NaHCO$_3$ solution and brine, dried (MgSO$_4$), filtered and concentrated to provide 275 mg of a residue. The residue was taken up in acetic acid (3 mL) and Zn powder (115 mg, 1.8 mmol) was added. The mixture was stirred at room temperature for 30 minutes and then heated to 120° C. for 2 hrs. After cooling to room temperature, the reaction mixture was filtered through diatomaceous earth, and washed with ethyl acetate. The filtrate was washed with H$_2$O and brine, dried (MgSO$_4$), filtered, and concentrated. The residue was chromatographed on silica gel eluting with 10% ethyl acetate in hexanes to provide the title compound as a colorless oil (59 mg). $^1$H NMR (300 MHz, CDCl$_3$) δ 3.16-3.27 (m, 2 H), 3.47-3.57 (m, 2 H), 3.66 (p, J=6 Hz, 1H), 6.98 (dd, J=9 Hz, J=3 Hz, 1 H), 7.07 (dd, J=9 Hz, J=3 Hz, 1 H), 7.53 (t, J=7.5 Hz, 1 H); (DCl/NH$_3$) m/z 243 (M+H)$^+$.

Example 22C 3-(4-Bromo-3-fluoro-phenyl)-cis-cyclobutanol

The title compound was prepared using the procedure described in Example 1A, substituting the product from Example 22B for 3-(4-bromo-phenyl)-cyclobutanone. $^1$H NMR (300 MHz, CDCl$_3$) δ 2.0 (m, 2 H), 2.78 (m, 2 H), 2.92 (p, J=6 Hz, 1H), 4.28 (p, J=6 Hz, 1H), 6.88 (dd, J=7.5 Hz, J=3 Hz, 1 H), 6.98 (dd, J=7.5 Hz, J=3 Hz, 1 H), 7.45 (t, J=7.5 Hz, 1 H); (DCl/NH$_3$) m/z 262 (M+NH$_4$)$^+$.

Example 22D

1-[3-(4-Bromo-3-fluoro-phenyl)-trans-cyclobutyl]-(2R)-2-methyl-pyrrolidine

The title compound was prepared using the procedure described in Example 1B except substituting the product from Example 22C for the product from Example 1A. $^1$H NMR (300 MHz, CD$_3$OD) δ 1.12 (d, J=6 Hz, 3 H), 1.48 (m, 1 H), 1.78 (m, 2 H), 2.00 (m, 1 H), 2.23 (m, 1 H), 2.36 (m, 2 H), 2.59 (m, 3 H), 3 H), 3.03 (m, 1 H), 3.34 (m, 1 H), 3.48 (m, 1 H), 7.06 (dd, J=9 Hz, J=3 Hz, 1 H), 7.17 (dd, J=9 Hz, J=3 Hz, 1 H), 7.53 (t, J=9 Hz, 1 H); (DCI/NH$_3$) m/z 312 (M+H)$^+$.

Example 22E

5-{2-Fluoro-4-[3-({2R}-2-methyl-pyrrolidin-1-yl)-trans-cyclobutyl]-phenyl}-pyrimidine

The title compound was prepared using the procedure described in Example 1C except substituting the product from Example 22D for the product from Example 1B and substituting pyrimidine-5-boronic acid for 4-cyanophenylboronic acid. $^1$H NMR (300 MHz, CD$_3$OD) δ 1.16 (d, J=6 Hz, 3 H), 1.50 (m, 1 H), 1.82 (m, 2 H), 2.05 (m, 1 H), 2.32 (m, 1 H), 2.45 (m, 2 H), 2.68 (m, 3 H), 3.09 (m, 1 H), 3.44 (m, 1 H), 3.60 (m, 1 H), 7.31 (t, J=9 Hz, 2 H), 7.58 (t, J=9 Hz, 1 H), 9.0 (s, 2 H), 9.14 (s, 1 H); (DCI/NH$_3$) m/z 312 (M+H)$^+$.

Example 23

4'-{3-[(2R)-2-Methyl-pyrrolidin-1-ylmethyl]-cis-cyclobutyl}-biphenyl-4-carbonitrile

Example 23A

3-(4-Bromo-phenyl)-trans-cyclobutanecarbaldehyde (A1) and 3-(4-bromo-phenyl)-cis-cyclobutanecarbaldehyde (A2)

To a solution of diethyl isocyanomethylphosphonate (0.86 mL, 5.3 mmol) in anhydrous ether (45 mL) at −78° C. under nitrogen was added n-butyl lithium (2.13 mL, 2.5 M in hexane) and the resulting mixture was stirred at −78° C. for 1 hr. Then, 3-(4-bromo-phenyl)-cyclobutanone (1 g, 4.4 mmol) in anhydrous ether (15 mL) was added dropwise over 30 minutes. The reaction mixture was allowed to warm to ambient temperature and stirred 16 hours. Concentrated hydrochloric acid (9.5 mL) was added dropwise and the reaction mixture was stirred at room temperature for 5 hrs. The mixture was partitioned between ethyl acetate and water. The layers were separated and the aqueous layer was extracted with ethyl acetate. The combined organic layers were washed with brine, dried (MgSO$_4$), filtered, and concentrated. The residue was chromatographed on silica gel eluting with 2-3% ethyl acetate in hexanes to provide 3-(4-bromo-phenyl)-trans-cyclobutanecarbaldehyde (281 mg, 27%) as the faster eluting isomer (A1) and 3-(4-bromo-phenyl)-cis-cyclobutanecarbaldehyde (508 mg, 48%) as the slower eluting isomer (A2). A1: $^1$H NMR (300 MHz, CDCl$_3$) δ 2.37 (m, 2 H), 2.72 (m, 2 H), 3.16 (m, 1 H), 3.53 (p, J=6 Hz, 1 H), 7.09 (d, J=9 Hz, 2 H), 7.44 (d, J=9Hz, 2 H), 9.95 (s, 1 H),; (DCI/NH$_3$) m/z 239 (M+H)$^+$; A2: $^1$ H NMR (300 MHz, CDCl$_3$) δ 2.35 (m, 2 H), 2.55 (m, 2 H), 3.21 (m, 1 H), 3.52 (p, J=6 Hz, 1 H), 7.07 (d, J=9 Hz, 2 H), 7.42 (d, J=9 Hz, 2 H), 9.73 (s, 1 H); (DCI/NH$_3$) m/z 239 (M+H)$^+$.

Example 23B

1-[3-(4-Bromo-phenyl)-cis-cyclobutylmethyl]-(2R)-2-methyl-pyrrolidine

A solution of the slower eluting isomer (A2) from Example 23A (508 mg, 2.1 mmol) in ethanol (15 mL) under nitrogen was treated with NaBH$_4$ (121 mg, 3.2 mmol) at 0° C., warmed to ambient temperature for 2 hrs and concentrated under reduced pressure. The residue was dissolved in ethyl acetate, washed with water, then washed with brine, and dried (MgSO$_4$), filtered, and concentrated. The residue was dissolved in dichloromethane (15 mL) and methanesulfonyl chloride (0.19 mL, 2.55 mmol) was added at 0° C., followed with triethylamine (0.43 mL, 3.2 mmol). The reaction was stirred at ambient temperature for 16 hours. The mixture was diluted with dichloromethane, washed with H$_2$O, dried (MgSO$_4$), filtered, and concentrated. The residue was chromatographed on silica gel eluting with ethyl acetate:dichloromethane:hexane (2:30:60) to provide the corresponding mesylate (326 mg). The obtained mesylate was dissolved in acetonitrile (15 mL). To this solution was added a solution of (R)-2-methylpyrrolidine (prepared according to the procedure that described in: R. Altenbach et al., WO 2004043458, and Y. Pu et al., Organic Process Research & Development, 9(1), 45-50, 2005) (230 mg, 2.07 mmol) in toluene, followed with K$_2$CO$_3$ (850 mg, 6.16 mmol). The reaction was heated to 65° C. and stirred 16 hours. Ethyl acetate (80 mL) was added and the mixture was washed with water, then washed with brine, and dried (MgSO$_4$), filtered, and concentrated. The residue was chromatographed on silica gel eluting with 2% (9:1 MeOH:concentrated NH$_4$OH) in dichloromethane to provide the title compound as a colorless oil (250 mg). $^1$H NMR (300 MHz, CD$_3$OD) δ 1.12 (d, J=6 Hz, 3 H), 1.40 (m, 1 H), 1.76 (m, 4 H), 1.94 (m, 1 H), 2.16 (m, 2 H), 2.32 (m, 1 H), 2.52 (m, 3 H), 2.93 (m, 1 H), 3.12 (m, 1 H), 3.36 (m, 1 H), 7.12 (d, J=9 Hz, 2 H), 7.40 (d, J=9 Hz, 2 H); (DCI/NH$_3$) m/z 308 (M+H)$^+$.

Example 23C

4'-{3-[(2R)-2-Methyl-pyrrolidin-1-ylmethyl]-cis-cyclobutyl}-biphenyl-4-carbonitrile

A solution of the product from Example 23B (30 mg, 0.1 mmol), 4-cyanophenylboronic acid (22 mg, 0.15 mmol), potassium carbonate (41 mg, 0.3 mmol) and dichlorobis(triphenylphosphine)palladium(II) (6 mg, 5 µmol) in isopropyl alcohol (2 mL) under an atmosphere of nitrogen was heated at 90° C. for 5 hrs. The reaction mixture was cooled to ambient temperature. Water (2 mL) was added and the mixture was extracted with ethyl acetate (5 mL). The organic layer was washed with brine, dried (MgSO$_4$), filtered and concentrated. The resulting oil was purified on preparative HPLC on a Waters™ Symmetry® C8 column (25 mm×100 mm, 7 µm particle size) using a gradient of 10% to 100% acetonitrile:0.1% aqueous TFA over 8 min (10 min run time) at a flow rate of 40 mL/min to provide 20 mg of the title compound as a trifluoroacetic acid salt. $^1$H NMR (300 MHz, CD$_3$OD) δ 1.46 (d, J=6 Hz, 3 H), 1.74 (m, 1 H), 2.08 (m, 4 H), 2.35 (m, 1 H), 2.68 (m, 3 H), 3.09 (m, 1 H), 3.18 (m, 1 H), 3.47 (m, 3 H), 3.68 (m, 1 H), 7.39 (d, J=9 Hz, 2 H), 7.62 (d, J=9 Hz, 2 H), 7.78 (s, 4 H); (DCI/NH$_3$) m/z 331 (M+H)$^+$.

Example 24

4'-{3-[(2R)-2-Methyl-pyrrolidin-1-ylmethyl]-trans-cyclobutyl}-biphenyl-4-carbonitrile

Example 24A

1-[3-(4-Bromo-phenyl)-trans-cyclobutylmethyl]-(2R)-2-methyl-pyrrolidine

The title compound was prepared using the procedure described in Example 23B substituting the faster eluting isomer (A1) from Example 23A for the slower eluting isomer (A2) from Example 23A. $^1$H NMR (300 MHz, CD$_3$OD) δ 1.18 (d, J=6 Hz, 3 H), 1.44 (m, 1 H), 1.79 (m, 2 H), 2.02 (m, 1 H), 2.27 (m, 7 H), 2.60 (m, 1 H), 3.13 (m, 2 H), 3.54 (m, 1 H), 7.20 (d, J=9 Hz, 2 H), 7.43 (d, J=9 Hz, 2 H); (DCl/NH$_3$) m/z 308 (M+H)$^+$.

Example 24B

4'-{3-[(2R)-2-Methyl-pyrrolidin-1-ylmethyl]-trans-cyclobutyl}-biphenyl-4-carbonitrile The trifluoroacetic acid salt of the title compound was prepared using the procedure described in Example 23C except substituting the product from Example 24A for the product from Example 23B. $^1$H NMR (300 MHz, CD$_3$OD) δ 1.48 (d, J=6 Hz, 3 H), 1.75 (m, 1 H), 2.10 (m, 2 H), 2.39 (m, 3 H), 2.48 (m, 2 H), 2.83 (m, 1 H), 3.22 (m, 2 H), 3.51 (m, 1 H), 3.67 (m, 3 H), 7.43 (d, J=9 Hz, 2 H), 7.66 (d, J=9 Hz, 2 H), 7.80 (s, 4 H), (DCl/NH$_3$) m/z 331 (M+H)$^+$.

Example 25

4'-{3-[(2S)-2-Methyl-pyrrolidin-1-ylmethyl]-cis-cyclobutyl}-biphenyl-4-carbonitrile Example 25A 1-[3-(4-bromo-phenyl)-cis-cyclobutylmethyl]-2-methyl-pyrrolidine The title compound was prepared using the procedure described in Example 23B except substituting (S)-2-methyl pyrrolidine for (R)-2-methyl pyrrolidine. $^1$H NMR (300 MHz, CD$_3$OD) δ 1.12 (d, J=6 Hz, 3 H), 1.40 (m, 1 H), 1.76 (m, 4 H), 1.94 (m, 1 H), 2.16 (m, 2 H), 2.32 (m, 1 H), 2.52 (m, 3 H), 2.93 (m, 1 H), 3.12 (m, 1 H), 3.36 (m, 1 H), 7.12 (d, J=9 Hz, 2 H), 7.40 (d, J=9 Hz, 2 H); (DCl/NH$_3$) m/z 308 (M+H)$^+$.

Example 25B

4'-{3-[(2S)-2-Methyl-pyrrolidin-1-ylmethyl]-cis-cyclobutyl}-biphenyl-4-carbonitrile The title compound was prepared using the procedure described in Example 23C except substituting the product from Example 25A for the product from Example 23B. The obtained trifluoroacetic acid salt was dissolved in water, treated with NaOH (10%), extracted with dichloromethane and separated. The organic was dried (MgSO$_4$), filtered, and concentrated to provide the title compound as a colorless oil. $^1$H NMR (300 MHz, CD$_3$OD) δ 1.25 (d, J=6 Hz, 3 H), 1.54 (m, 1 H), 1.89 (m, 5 H), 2.12 (m, 1 H), 2.61 (m, 5 H), 3.15 (m, 2 H), 3.50 (m, 1 H), 7.35 (d, J=9 Hz, 2 H), 7.63 (d, J=9 Hz, 2 H), 7.79 (s, 4 H); (DCl/NH$_3$) m/z 331 (M+H)$^+$.

Example 26

2,6-Difluoro-3-{4-[3-(2-methyl-pyrrolidin-1-ylmethyl)-cis-cyclobutyl]-phenyl}-pyridine The trifluoroacetic acid salt of the title compound was prepared using the procedure described in Example 23C except substituting 2,6-difluoropyridine-3-boronic acid (CAS # 136466-94-9) for 4-cyanophenylboronic acid. $^1$H NMR (300 MHz, CD$_3$OD) δ 1.46 (d, J=6 Hz, 3 H), 1.73 (m, 1 H), 2.07 (m, 4 H), 2.33 (m, 1 H), 2.68 (m, 3 H), 3.09 (m, 1 H), 3.18 (m, 1 H), 3.45 (m, 2 H), 3.57 (m, 1 H), 3.67 (m, 1 H), 7.07 (dd, J=9 Hz, J=3 Hz, 1 H), 7.37 (d, J=9 Hz, 2 H), 7.51 (dd, J=9 Hz, J=3 Hz, 2 H), 8.14 (dd, J=12 Hz, J=6 Hz, 1 H); (DCl/NH$_3$) m/z 343 (M+H)$^+$.

Example 27

5-{4-[3-(2-Methyl-pyrrolidin-1-ylmethyl)-cis-cyclobutyl]-phenyl}-pyrimidine

The trifluoroacetic acid salt of the title compound was prepared using the procedure described in Example 23C except substituting 5-pyrimidineboronic acid (CAS # 109299-78-7) for 4-cyanophenylboronic acid. $^1$H NMR (300 MHz, CD$_3$OD) δ 1.46 (d, J=6 Hz, 3 H), 1.74 (m, 1 H), 2.07 (m, 4 H), 2.33 (m, 1 H), 2.69 (m, 3 H), 3.08 (m, 1 H), 3.19 (m, 1 H), 3.45 (m, 2 H), 3.58 (m, 1 H), 3.68 (m, 1 H), 7.43 (d, J=9 Hz, 2 H), 7.68 (d, J=9 Hz, 2 H), 9.05 (s, 2 H), 9.12 (s, 1 H); (DCl/NH$_3$) m/z 308 (M+H)$^+$.

Example 28

4'-[3-(2-Methyl-pyrrolidin-1-ylmethyl)-cis-cyclobutyl]-biphenyl-4-carbonitrile

Example 28A

1-[3-(4-bromo-phenyl)-cis-cyclobutylmethyl]-2-methyl-pyrrolidine

The title compound was prepared using the procedure described in Example 23B except substituting 2-methyl pyrrolidine for (R)-2-methyl pyrrolidine.

Example 28B

4'-[3-(2-Methyl-pyrrolidin-1-ylmethyl)-cis-cyclobutyl]-biphenyl-4-carbonitrile

The title compound was prepared using the procedure described in Example 23C, except substituting the product from Example 28A for the product from Example 23B. The obtained trifluoroacetic acid salt was dissolved in water, treated with NaOH (10%), extracted with dichloromethane, and separated. The organic layer was dried (MgSO$_4$), filtered, and concentrated to provide the title compound as a colorless oil. $^1$H NMR (300 MHz, CD$_3$OD) δ 1.32 (d, J=6 Hz, 3 H), 1.62 (m, 1 H), 1.96 (m, 4 H), 2.18 (m, 1 H), 2.59 (m, 3 H), 2.79 (m, 1 H), 3.05 (m, 1 H), 3.24 (m, 2 H), 3.45 (m, 1 H), 3.52 (m, 1 H), 7.36 (d, J=9 Hz, 2 H), 7.63 (d, J=9 Hz, 2 H), 7.78 (s, 4 H); (DCl/NH$_3$) m/z 331 (M+H)$^+$.

Example 29

1,3,5-Trimethyl-4-{4-[3-({2R}-2-methyl-pyrrolidin-1-ylmethyl)-cis-cyclobutyl]-phenyl}-1H-pyrazole The title compound was prepared using the procedure described in Example 23C substituting the product from Example 21A for 4-cyanophenylboronic acid. The obtained trifluoroacetic acid salt was dissolved in water, treated with NaOH (10%), extracted with dichloromethane and separated. The organic was dried (MgSO$_4$), filtered and concentrated to provide the title compound as a colorless oil. $^1$H NMR (300 MHz, CD$_3$OD) δ 1.14 (d, J=6 Hz, 3 H), 1.44 (m, 1 H), 1.80 (m, 4 H), 1.96 (m, 1 H), 2.15 (s, 3 H), 2.18 (m, 2 H), 2.22 (s, 3 H), 2.36 (m, 1 H), 2.55 (m, 3 H), 2.95 (m, 1 H), 3.16 (m, 1 H), 3.43

(m, 1 H), 3.74 (s, 3 H), 7.16 (d, J=9 Hz, 2 H), 7.26 (d, J=9 Hz, 2 H); (DCl/NH$_3$) m/z 338 (M+H)$^+$.

Example 30

2-{4-[3-({2R}-2-Methyl-pyrrolidin-1-ylmethyl)-cis-cyclobutyl]-phenyl}-2H-pyridazin-3-one A solution of the product from Example 23B (49 mg, 0.16 mmol), 2H-pyridazin-3-one (30 mg, 0.3 mmol), trans-(1R, 2R)-N,N'-bismethyl-1,2-cyclohexane diamine (45 mg, 0.32 mmol), CuI (30 mg, 0.16 mmol), and K$_2$CO$_3$ (65 mg, 0.48 mmol) in dioxane (3 mL) was heated in a microwave reactor to 190° C. for 5 hrs. The reaction mixture was cooled to ambient temperature and diluted with ethyl acetate (25 mL). The mixture was washed with H$_2$O, brine, dried with magnesium sulfate, filtered, and concentrated. The residue was chromatographed on silica gel eluting with a gradient of 2-5% (9:1 MeOH:concentrated NH$_4$OH) in dichloromethane/ethyl acetate/hexanes (1:1:1) to provide 20 mg of the title compound. $^1$H NMR (300 MHz, CD$_3$OD) δ 1.45 (d, J=6 Hz, 3 H), 1.73 (m, 1 H), 2.07 (m, 4 H), 2.33 (m, 1 H), 2.68 (m, 3 H), 3.09 (m, 1 H), 3.19 (m, 1 H), 3.45 (m, 2 H), 3.64 (m, 2 H), 7.08 (dd, J=9 Hz, J=3 Hz, 1 H), 7.38 (d, J=9 Hz, 2 H), 7.49 (m, 3 H), 7.08 (dd, J=3 Hz, J=1 Hz, 1 H); (DCl/NH$_3$) m/z 324 (M+H)$^+$.

Example 31

2-Methoxy-5-{4-[3-({2R}-2-methyl-pyrrolidin-1-ylmethyl)-cis-cyclobutyl]-phenyl}-pyrimidine The title compound was prepared using the procedure described in Example 23C except substituting 2-methoxy-5-pyrimidineboronic acid (Frontier Scientific, Inc., Logan, Utah, USA) for 4-cyanophenylboronic acid. The obtained trifluoroacetic acid salt was dissolved in water, treated with NaOH (10%), extracted with dichloromethane and separated. The organic was dried (MgSO$_4$), filtered and concentrated to provide the title compound as a colorless oil. $^1$H NMR (300 MHz, CD$_3$OD) δ 1.32 (d, J=6 Hz, 3 H), 1.61 (m, 1 H), 1.95 (m, 4 H), 2.17 (m, 1 H), 2.64 (m, 5 H), 3.04 (m, 1 H), 3.23 (m, 1 H), 3.44 (m, 1 H), 3.53 (m, 1 H), 4.95 (s, 3 H), 7.36 (d, J=9 Hz, 2 H), 7.57 (d, J=9 Hz, 2 H), 8.80 (s, 2 H); (DCl/NH$_3$) m/z 338 (M+H)$^+$.

Example 32

2,4-Dimethoxy-5-{4-[3-({2R}-2-methyl-pyrrolidin-1-ylmethyl)-cis-cyclobutyl]-phenyl}-pyrimidine The title compound was prepared using the procedure described in Example 23C except substituting 2,4-dimethoxy-5-pyrimidineboronic acid (CAS # 89641-18-9) for 4-cyanophenylboronic acid. The obtained trifluoroacetic acid salt was dissolved in water, treated with NaOH (10%), extracted with dichloromethane and separated. The organic was dried (MgSO$_4$), filtered and concentrated to provide the title compound as a colorless oil. $^1$H NMR (300 MHz, CD$_3$OD) δ 1.14 (d, J=6 Hz, 3 H), 1.42 (m, 1 H), 1.77 (m, 4 H), 1.96 (m, 1 H), 2.19 (m, 2 H), 2.34 (m, 1 H), 2.55 (m, 3 H), 2.94 (m, 1 H), 3.15 (m, 1 H), 3.43 (m, 1 H), 4.03 (s, 6 H), 7.26 (d, J=9 Hz, 2 H), 7.42 (d, J=9 Hz, 2 H), 8.23(s, 1 H); (DCl/NH$_3$) m/z 368 (M+H)$^+$.

Example 33

4'-{3-[(2R)-2-Methyl-pyrrolidin-1-yl]-cis-cyclobutylmethyl}-biphenyl-4-carbonitrile

Example 33A 3-(4-Bromo-benzyl)-2,2-dichloro-cyclobutanone

To a solution of 1-allyl-4-bromo-benzene (400 mg, 2 mmol) and activated Zn—Cu (200 mg, 3 mmol) in anhydrous ether (30 mL) was added dropwise a mixture of phosphorus oxychloride (0.3 mL, 3.2 mmol) and trichloroacetyl chloride (0.34 mL, 3 mol) in anhydrous ether (10 mL). After the addition, the reaction was stirred at room temperature overnight. The reaction mixture was filtered through diatomaceous earth and washed with ether. The ethereal solution was concentrated in vacuo to ca. ¼ of its original volume. Pentane (100 mL) was added and the solution stirred for a few minutes to precipitate the zinc salts. The solution was decanted from the residue, washed successively with H$_2$O, a cold saturated NaHCO$_3$ solution and brine, dried (MgSO$_4$), filtered and concentrated to provide 275 mg of a residue. Chromatography of the residue on silica gel eluting with 6% ethyl acetate in hexanes afforded the title compound as the white solid (115 mg, 18%). $^1$H NMR (300 MHz, CDCl3) δ 2.8 (dd, J=15 Hz, J=6 Hz, 1 H), 3.05 (dd, J=15 Hz, J=6 Hz, 1 H), 3.18 (m, 1 H), 3.30 (m, 2 H), 7.12 (d, J=9 Hz, 2 H), 7.46 (d, J=9 Hz, 2 H); (DCl/NH$_3$) m/z 308(M+H)$^+$.

Example 33B 3-(4-Bromo-benzyl)-cyclobutanone

A solution of the product from Example 33A (115 mg, 0.37 mmol) in acetic acid (4 mL) was treated with Zn powder (60 mg, 0.93 mm) at room temperature and stirred for 1 hr and then heated to 120° C. for 2 hrs. The reaction mixture was cooled to room temperature, filtered through a layer of diatomaceous earth and washed with ethyl acetate. The filtrate was washed with H$_2$O, brine, dried (MgSO$_4$), filtered and concentrated. The residue was chromatographed on silica gel eluting with 10% ethyl acetate in hexanes to provide the title compound as a white solid (82 mg, 95%). $^1$H NMR (300 MHz, CD$_3$OD) δ 2.66-2.81 (m, 3 H), 2.86 (d, J=6 Hz, 2 H), 3.08-3.19 (m, 2 H), 7.06 (d, J=9 Hz, 2 H), 7.43 (d, J=9 Hz, 2 H); (DCl/NH$_3$) m/z 239(M+H)$^+$.

Example 33C

1-[3-(4-Bromo-benzyl)-cis-cyclobutyl]-(2R)-2-methyl-pyrrolidine

To a solution of the product from Example 33B (80 mg, 0.34 mmol) in ethanol (8 mL) was added (R)-2-methylpyrrolidine (prepared according to the procedure that described in: R. Altenbach et al., WO 2004043458, and Y. Pu et al., Organic Process Research & Development, 9(1), 45-50, 2005) (57 mg, 0.67 mmol) in toluene (3 mL) followed with dropwise addition of borane-pyridine complex (52 μl, 0.51 mmol) in ethanol (2 mL). The reaction was stirred at room temperature for 3 hrs and concentrated under reduced pressure. The resulting residue was chromatographed on silica gel eluting with a gradient of 1% to 2% (9:1 MeOH:concentrated NH$_4$OH) in dichloromethane to provide the title compound (45 mg) and the corresponding trans isomer (19 mg). $^1$H NMR (300 MHz, CD$_3$OD) δ 1.17 (d, J=6 Hz, 3 H), 1.50 (m, 1 H), 1.70 (m, 4 H), 2.04 (m, 1 H), 2.27 (m, 3 H), 2.46 (m, 1 H), 2.68 (d, J=6 Hz, 2 H), 2.70(m, 1 H), 3.07 (m, 2 H), 7.07 (d, J=9 Hz, 2 H), 7.39 (d, J=9 Hz, 2 H); (DCI/NH$_3$) m/z 308, 310.

Example 33D

4'-{3-[(2R)-2-Methyl-pyrrolidin-1-yl]-cis-cyclobutylmethyl}-biphenyl-4-carbonitrile The title compound was prepared using the procedure described in Example 1C except substituting the product from Example 33C for the product from Example 1B. $^1$H NMR (300 MHz, CD$_3$OD) δ 1.24 (d, J=6 Hz, 3 H), 1.60 (m, 1 H), 1.86 (m, 4 H), 2.14 (m, 1 H), 2.35 (m, 3 H), 2.66 (m, 1 H), 2.79 (d, J=6 Hz, 2 H), 2.81 (m, 1 H), 3.21 (m, 2 H), 7.30 (d, J=9 Hz, 2 H), 7.60 (d, J=9 Hz, 2 H), 7.78 (s, 4 H); (DCI/NH$_3$) m/z 331 (M+H)$^+$.

Example 34

Determination of Biological Activity

To determine the effectiveness of representative compounds of this invention as histamine-3 receptor ligands (H$_3$ receptor ligands), the following tests were conducted according to methods previously described (European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid N$_2$ and stored at −70° C. until used in assays. Rat cortical membranes (12 mg wet weight/tube) were incubated with ($^3$H)-N-α-methylhistamine (~0.6 nM) with or without H$_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 µM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and K$_i$ values were determined using the Cheng-Prusoff equation.

Generally, representative compounds of the invention demonstrated binding affinities in the above assay from about 0.05 nM to about 150 nM. Preferred compounds of the invention bound to histamine-3 receptors with binding affinities from about 0.05 nM to about 10 nM. More preferred compounds of the invention bound to histamine-3 receptors with binding affinities from about 0.05 nM to about 0.2 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula:

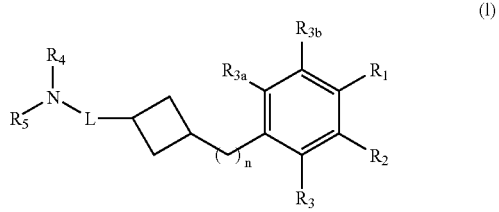

or a pharmaceutically acceptable salt, ester, or amide thereof, wherein:
one of R$_1$ and R$_2$ is a group of the formula -L$_2$-R$_{6a}$-L$_3$-R$_{6b}$;
the other of R$_1$ and R$_2$ is selected from the group consisting of hydrogen, alkyl, alkoxy, halogen, cyano, and thioalkoxy;
R$_3$, R$_{3a}$, and R$_{3b}$ are each independently selected from the group consisting of hydrogen, alkyl, alkoxy, halogen, cyano, and thioalkoxy;
R$_4$ and R$_5$ are each independently selected from the group consisting of alkyl, fluoroalkyl, hydroxyalkyl, alkoxyalkyl, and cycloalkyl, or R$_4$ and R$_5$ taken together with the nitrogen atom to which each is attached form a non-aromatic ring of the formula:

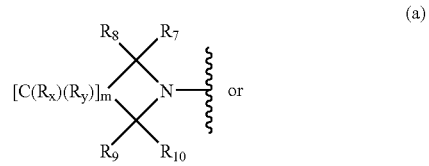

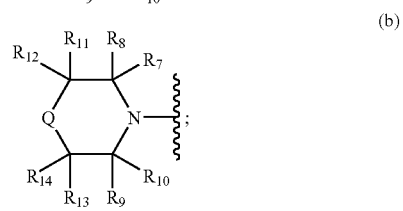

$R_7$, $R_8$, $R_9$, and $R_{10}$ at each occurrence are each independently selected from the group consisting of hydrogen, hydroxyalkyl, fluoroalkyl, cycloalkyl, and alkyl;

$R_{11}$, $R_{12}$, $R_{13}$, and $R_{14}$ are each independently selected from the group consisting of hydrogen, hydroxyalkyl, alkyl, and fluoroalkyl;

$R_{6a}$ is a 5- to 6-membered heteroaryl ring, or an 8- to 10-membered bicyclic heteroaryl ring;

$R_{6b}$ is hydrogen,

Q is O or S;

L is —$[C(R_{16})(R_{17})]_k$;

$L_2$ is a bond;

$L_3$ is a bond;

$R_{16}$ and $R_{17}$ at each occurrence are independently selected from the group consisting of hydrogen and alkyl;

$R_x$ and $R_y$ at each occurrence are independently selected from the group consisting of hydrogen, hydroxy, alkyl, alkoxy, alkylamino, fluoro, and dialkylamino;

k is 0, 1, or 2;

m is an integer from 1 to 5; and n is 0 or 1.

2. The compound of claim 1, wherein $R_1$ is -$L_2$-$R_{6a}$-$L_3$-$R_{6b}$, wherein $L_2$ is a bond, $R_{6b}$ is hydrogen, $L_3$ is a bond, and $R_{6a}$ is selected from a 5- or 6-membered heteroaryl ring.

3. The compound of claim 2, wherein $R_{6a}$ is an unsubstituted or substituted ring selected from the group consisting of furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,4]thiadiazolonyl, [1,2,5]thiadiazolonyl, [1,3,4]thiadiazinonyl, [1,2,3]oxadiazolyl, [1,2,4]oxadiazolonyl, [1,2,5]oxadiazolonyl, [1,3,4]oxadiazin-onyl, thiazolyl, thienyl, [1,2,3]triazinyl, [1,2,4]triazinyl, [1,3,5]triazinyl, [1,2,3]triazolyl, [1,2,4]triazolyl, pyridazinonyl, pyridonyl, and pyrimidinonyl.

4. The compound of claim 2, wherein $R_{6a}$ is an unsubstituted or substituted heteroaryl ring selected from the group consisting of pyrimidinyl, pyridazinonyl, pyridinyl, and pyrazolyl.

5. The compound of claim 1, wherein $R_1$ is -$L_2$-$R_{6a}$-$L_3$-$R_{6b}$, wherein $L_2$ is a bond, $R_{6b}$ is hydrogen, $L_3$ is a bond, and $R_{6a}$ is selected from a 8- to 10-membered bicyclic heteroaryl ring.

6. The compound of claim 5, wherein $R_{6a}$ is an unsubstituted or substituted ring selected from the group consisting of indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, and pyrrolopyrimidinyl.

7. The compound of claim 6, wherein $R_{6a}$ is unsubstituted or substituted benzothiazolyl.

8. The compound of claim 1, wherein one of $R_3$, $R_{3a}$, and $R_{3b}$ is halogen and the others are hydrogen.

9. The compound of claim 1, wherein $R_4$ and $R_5$ taken together with the nitrogen atom to which each is attached form a 4- to 8-membered non-aromatic ring represented by formula (a).

10. The compound of claim 9, wherein at least one substituent represented by $R_7$, $R_8$, $R_9$, and $R_{10}$ is selected from the group consisting of alkyl, fluoroalkyl, and hydroxyalkyl or at least one substituent represented by $R_x$ or $R_y$ is alkyl, fluoro, or hydroxy.

11. The compound of claim 1, wherein $R_4$ and $R_5$ are taken together with the nitrogen atom to which each is attached to form a (2R)-methylpyrrolidine ring or (2S)-methylpyrrolidine ring.

12. The compound of claim 1, wherein the compound has the formula

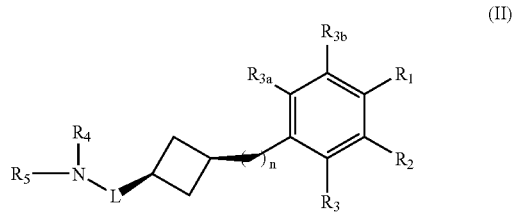

(II)

wherein L, n, $R_1$, $R_2$, $R_3$, $R_{3a}$, $R_{3b}$, $R_4$, and $R_5$ are each as defined in claim 1.

13. The compound of claim 12, wherein $R_1$ is -$L_2$-$R_{6a}$-$L_3$-$R_{6b}$, wherein $L_2$ is a bond, $R_{6b}$ is hydrogen, $L_3$ is a bond, $R_{6a}$ is selected from a 5- or 6-membered heteroaryl ring, and $R_4$ and $R_5$ taken together with the nitrogen atom to which each is attached form a 4- to 8-membered non-aromatic ring represented by formula (a).

14. The compound of claim 1, wherein the compound has the formula

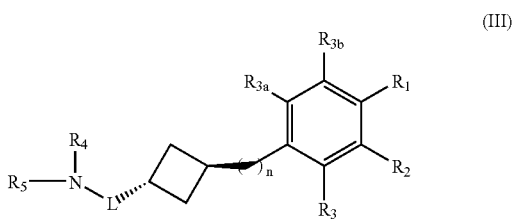

(III)

wherein L, n, $R_1$, $R_2$, $R_3$, $R_{3a}$, $R_{3b}$, $R_4$, and $R_5$ are each as defined in claim 1.

15. The compound of claim 14, wherein $R_1$ is -$L_2$-$R_{6a}$-$L_3$-$R_{6b}$, wherein $L_2$ is a bond, $R_{6b}$ is hydrogen, $L_3$ is a bond, $R_{6a}$ is selected from a 5- or 6-membered heteroaryl ring, and $R_4$ and $R_5$ taken together with the nitrogen atom to which each is attached form a 4- to 8-membered non-aromatic ring represented by formula (a).

16. The compound of claim 1, selected from the group consisting of

5-{4-[3-({2R}-2-methyl-pyrrolidin-1-yl)-cis-cyclobutyl]-phenyl}-pyrimidine;

2,6-difluoro-3-{4-[3-({2R}-2-methyl-pyrrolidin-1-yl)-cis-cyclobutyl]-phenyl}-pyridine;

2,6-difluoro-3-{4-[3-({2R}-2-methyl-pyrrolidin-1-yl)-trans-cyclobutyl]-phenyl}-pyridine;

2,6-dimethyl-3-{4-[3-({2R}-2-methyl-pyrrolidin-1-yl)-trans-cyclobutyl]-phenyl}-pyridine;

2,6-dichloro-3-{4-[3-({2R}-2-methyl-pyrrolidin-1-yl)-trans-cyclobutyl]-phenyl}-pyridine;

5-{4-[3-({2R}-2-methyl-pyrrolidin-1-yl)-trans-cyclobutyl]-phenyl}-pyrimidine;

2-{4-[3-({2R}-2-methyl-pyrrolidin-1-yl)-trans-cyclobutyl]-phenyl}-2H-pyridazin-3-one;

5-{4-[3-({2S}-2-methyl-pyrrolidin-1-yl)-trans-cyclobutyl]-phenyl}-pyrimidine;

2,4-dimethoxy-5-{4-[3-({2S}-2-methyl-pyrrolidin-1-yl)-trans-cyclobutyl]-phenyl}-pyrimidine;

2-methoxy-5-{4-[3-({2R}-2-methyl-pyrrolidin-1-yl)-trans-cyclobutyl]-phenyl}-pyrimidine;

2,4-dimethoxy-5-{4-[3-({2R}-2-methyl-pyrrolidin-1-yl)-trans-cyclobutyl]-phenyl}-pyrimidine;

5-{4-[3-({2R}-2-methyl-pyrrolidin-1-yl)-trans-cyclobutyl]-phenyl}-nicotinonitrile;

2-methyl-5-{4-[3-({2R}-2-methyl-pyrrolidin-1-yl)-trans-cyclobutyl]-phenyl}-benzothiazole;

2-methyl-5-{4-[3-({2R}-2-methyl-pyrrolidin-1-yl)-trans-cyclobutyl]-phenyl}-pyridine;

1,3,5-trimethyl-4-{4-[3-(2-methyl-pyrrolidin-1-yl)-trans-cyclobutyl]-phenyl}-1H-pyrazole;

5-{2-fluoro-4-[3-({2R}-2-methyl-pyrrolidin-1-yl)-trans-cyclobutyl]-phenyl}-pyrimidine;

2,6-difluoro-3-{4-[3-(2-methyl-pyrrolidin-1-ylmethyl)-cis-cyclobutyl]-phenyl}-pyridine;

5-{4-[3-(2-methyl-pyrrolidin-1-ylmethyl)-cis-cyclobutyl]-phenyl}-pyrimidine;

1,3,5-trimethyl-4-{4-[3-({2R}-2-methyl-pyrrolidin-1-ylmethyl)-cis-cyclobutyl]-phenyl}-1H-pyrazole;

2-{4-[3-({2R}-2-methyl-pyrrolidin-1-ylmethyl)-cis-cyclobutyl]-phenyl}-2H-pyridazin-3-one;

2-methoxy-5-{4-[3-({2R}-2-methyl-pyrrolidin-1-ylmethyl)-cis-cyclobutyl]-phenyl}-pyrimidine; and 2,4-dimethoxy-5-{4-[3-({2R}-2-methyl-pyrrolidin-1-ylmethyl)-cis-cyclobutyl]-phenyl}-pyrimidine.

17. A pharmaceutical composition comprising a therapeutically effective amount of a compound of claim 1 in combination with a pharmaceutically acceptable carrier.

\* \* \* \* \*